United States Patent
Kovach et al.

(10) Patent No.: US 10,532,050 B2
(45) Date of Patent: Jan. 14, 2020

(54) FORMULATIONS OF OXABICYCLOHEPTANES AND OXABICYCLOHEPTENES

(71) Applicant: Lixte Biotechnology, Inc., East Setauket, NY (US)

(72) Inventors: John S. Kovach, East Setauket, NY (US); Mickey L. Wells, Iowa City, IA (US)

(73) Assignee: Lixte Biotechnology, Inc., East Setauket, NY (US)

(*) Notice: Subject to any disclaimer, the term of this patent is extended or adjusted under 35 U.S.C. 154(b) by 88 days.

(21) Appl. No.: 14/783,360

(22) PCT Filed: Apr. 8, 2014

(86) PCT No.: PCT/US2014/033317
§ 371 (c)(1),
(2) Date: Oct. 8, 2015

(87) PCT Pub. No.: WO2014/168941
PCT Pub. Date: Oct. 16, 2014

(65) Prior Publication Data
US 2016/0051544 A1   Feb. 25, 2016

Related U.S. Application Data

(60) Provisional application No. 61/810,053, filed on Apr. 9, 2013.

(51) Int. Cl.
| | | |
|---|---|---|
| *A61K 31/496* | (2006.01) | |
| *A61K 31/34* | (2006.01) | |
| *A61K 31/4525* | (2006.01) | |
| *A61K 31/197* | (2006.01) | |
| *A61K 9/00* | (2006.01) | |

(52) U.S. Cl.
CPC .......... *A61K 31/496* (2013.01); *A61K 9/0019* (2013.01); *A61K 31/197* (2013.01); *A61K 31/34* (2013.01); *A61K 31/4525* (2013.01)

(58) Field of Classification Search
CPC .............. A61K 2300/00; A61K 31/197; A61K 31/4525; A61K 31/496; A61K 9/0019
USPC .................................................. 514/254.11
See application file for complete search history.

(56) References Cited

U.S. PATENT DOCUMENTS

| | | | | |
|---|---|---|---|---|
| 4,518,696 | A * | 5/1985 | Gehrman | C12N 1/04 424/93.45 |
| 4,760,067 | A * | 7/1988 | Firestone | C07C 317/00 435/183 |
| 5,565,435 | A * | 10/1996 | Yoneyama | A61K 8/602 435/75 |
| 5,580,856 | A * | 12/1996 | Prestrelski | A61K 38/2013 514/1.1 |
| 5,580,858 | A * | 12/1996 | Ippolito | A61K 31/70 514/25 |
| 7,998,957 | B2 * | 8/2011 | Kovach | C07D 493/08 514/231.5 |
| 8,058,268 | B2 | 11/2011 | Kovach | |
| 8,143,445 | B2 | 3/2012 | Kovach et al. | |
| 8,227,473 | B2 | 7/2012 | Kovach et al. | |
| 8,329,719 | B2 | 12/2012 | Kovach | |
| 8,426,444 | B2 | 4/2013 | Kovach et al. | |
| 8,455,688 | B2 | 6/2013 | Kovach et al. | |
| 8,541,458 | B2 | 9/2013 | Kovach et al. | |
| 8,685,436 | B2 * | 4/2014 | Ley | A23F 3/405 424/439 |
| 8,822,461 | B2 | 9/2014 | Kovach et al. | |
| 8,840,924 | B2 * | 9/2014 | Tengler | A61K 9/0056 424/464 |
| 9,079,917 | B2 * | 7/2015 | Kovach | C07D 493/08 |
| 9,994,584 | B2 * | 6/2018 | Piotrowski | C07D 493/08 |
| 2010/0029484 | A1 | 2/2010 | Kovach | |
| 2011/0287537 | A1 * | 11/2011 | Kovach | A61K 31/167 435/375 |
| 2014/0235649 | A1 | 8/2014 | Kovach et al. | |
| 2015/0148353 | A1 | 5/2015 | Kovach | |
| 2015/0174123 | A1 | 6/2015 | Kovach | |
| 2016/0264593 | A1 | 9/2016 | Kovach et al. | |
| 2016/0303115 | A1 | 10/2016 | Kovach et al. | |
| 2016/0333024 | A1 | 11/2016 | Kovach | |
| 2017/0136008 | A1 | 5/2017 | Kovach et al. | |

FOREIGN PATENT DOCUMENTS

| | | | |
|---|---|---|---|
| WO | WO 2007/092414 | A2 | 8/2007 |
| WO | WO 2008/097561 | A1 | 8/2008 |
| WO | WO 2009/020565 | A1 | 2/2009 |
| WO | WO 2009/045440 | A1 | 4/2009 |
| WO | WO 2010/014141 | A1 | 2/2010 |
| WO | WO 2010/014220 | A1 | 2/2010 |
| WO | WO 2010/014254 | A1 | 2/2010 |
| WO | WO 2010/147612 | A1 | 12/2010 |
| WO | WO 2012/162535 | A1 | 11/2012 |
| WO | WO 2014/005080 | A1 | 1/2014 |
| WO | WO 2014/005084 | A1 | 1/2014 |
| WO | WO 2014/137741 | A1 | 9/2014 |
| WO | WO 2014/149494 | A1 | 9/2014 |
| WO | WO 2014/168941 | A1 | 10/2014 |
| WO | WO 2015/073802 | A1 | 5/2015 |
| WO | WO 2015/196073 | A1 | 12/2015 |
| WO | WO 2016/014783 | A1 | 1/2016 |
| WO | WO 2016/040877 | A1 | 3/2016 |
| WO | WO 2016/061193 | A1 | 4/2016 |
| WO | WO 2016/134257 | A1 | 8/2016 |

OTHER PUBLICATIONS

Arakawat et al. (The Journal of Biological Chemistry, vol. 239m No. 8, Issue of Apr. 22, pp. 4979-4986, 1984).*

(Continued)

*Primary Examiner* — Sabiha N Qazi
(74) *Attorney, Agent, or Firm* — Andrea L. C. Reid; Dechert LLP

(57) ABSTRACT

The invention relates to a pharmaceutical composition comprising a protein phosphatase 2A (PP2A) inhibitor and monosodium glutamate.

12 Claims, 1 Drawing Sheet

(56) References Cited

OTHER PUBLICATIONS

Sunny-Roberts et al. (International Dairy Journal 19 (2009) 209-214).*

Vincent S. Stoll et al. (Chapter 6, Methods in Enzymology, vol. 463, 1990, Academic Press, ISSN 0076-6879). (Year: 1990).*

Communication Pursuant to Rules 70(2) and 70a(2) dated Nov. 21, 2016 in connection with European Patent Application No. 14783185.3.

Office Action dated Mar. 16, 2017 in connection with Chinese Patent Application No. 201480027136.9 (including English language translation).

Difeo, "Drug product development: A technical review of chemistry, manufacturing, and controls information for the support of pharmaceutical compound licensing activities," Drug Development and Industrial Pharmacy, 29(9):939-958, Aug. 2003.

Jain, "Theory and Practice of Physical Pharmacy," Elsevier India, 1st Ed. E-Book, Jan. 2013, pp. 150-154.

Lu et al., "The effect of a PP2A inhibitor on the nuclear receptor corepressor pathway in glioma," Journal of Neurosurgery, vol. 113, No. 2, pp. 225-233, Aug. 2010.

Martiniova et al., "Pharmacologic Modulation of Serine/Threonine Phosphorylation Highly Sensitizes PHEO in a MPC Cell and Mouse Model to Conventional Chemotherapy," PLoS ONE, vol. 6, No. 2, 8 pages, Feb. 2011.

Zhang et al., "The synthetic cantharidin analog for the enhancement of doxorubicin suppression of stem-cell derived aggressive sarcoma," Biomaterials, vol. 31, No. 36, pp. 9535-9543, Dec. 2010.

Office Action dated Aug. 17, 2016 in connection with Chinese Patent Application No. 201480027138.9 including English language translation provided by Chinese agent.

International Search Report dated Aug. 25, 2014 in connection with PCT International Application No. PCT/US14/33317.

Written Opinion of the International Searching Authority dated Aug. 25, 2014 in connection with PCT International Application No. PCT/US14/33317.

International Preliminary Report on Patentability Chapter I dated Oct. 13, 2015 in connection with PCT International Application No. PCT/US14/33317.

* cited by examiner

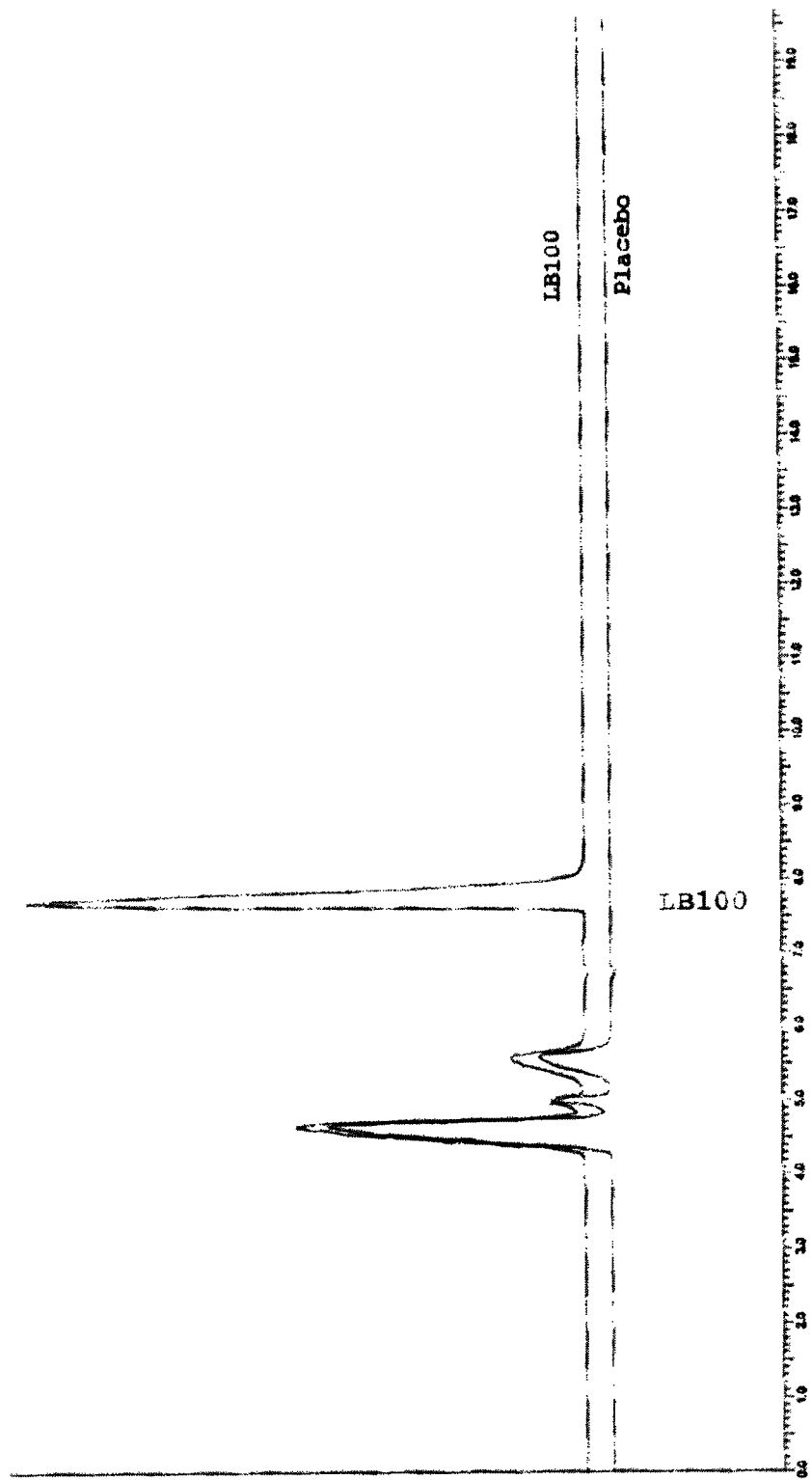

FORMULATIONS OF OXABICYCLOHEPTANES AND OXABICYCLOHEPTENES

This application is a § 371 national stage of PCT International Application No. PCT/US2014/033317, filed Apr. 8, 2014 claiming the benefit of U.S. Provisional Application No. 61/810,053, filed Apr. 9, 2013, the contents of each of which are hereby incorporated by reference in their entirety.

Throughout this application various publications are referenced. The disclosures of these documents in their entireties are hereby incorporated by reference into this application in order to more fully describe the state of the art to which this invention pertains.

BACKGROUND OF THE INVENTION

PCT International Application Publication Nos. WO 2008/097561, WO 2009/020565, WO 2010/014141, WO 2010/014220, WO 2010/014254, WO 2010/147612, and WO 2012/162535 describe small molecule protein phosphatase 2A (PP2A) inhibitors and their use for treating a variety of conditions including cancers, neurodegenerative diseases, and diseases characterized by loss of protein function.

One of the PP2A inhibitors described in PCT International Application Publication No. WO 2008/097561, LB-100, has shown antiproliferative activity as a single agent and in combination with other cytotoxic agents against cancer cells in vitro and against tumor xenografts in in vivo animal models. For example, LB-100 was shown to inhibit the growth of glioblastoma multiforme (GBM) xenograft cells (Lu et al., J. Neurosurg. 113:225-233 (2010)), increase the effectiveness of the standard anti-sarcoma chemotherapeutic agent doxorubicin in a rat fibrosarcoma model (Zhang et al., Biomaterials vol. 31(36):9535-43 (2010)), and delay tumor growth when administered with temozolomide (TMZ) in a mouse model of metastatic pheochromocytoma (PHEO) (Martiniova et al., Plos One, vol. 6(2):e14678 (2011)).

To date, the PP2A inhibitors described in PCT International Application Publication Nos. WO 2008/097561, WO 2009/020565, WO 2010/014141, WO 2010/014220, WO 2010/014254, WO 2010/147612, and WO 2012/162535 have not been explored in human clinical trials. However, LB-100 has been approved by the Food and Drug Administration for Phase I study in patients with advanced cancers given alone and then in combination with the widely used anticancer drug docetaxel.

Accordingly, there is a need for pharmaceutical compositions comprising PP2A inhibitors, and LB-100 in particular, which are suitable for administration to human subjects in, for example, clinical trials. Such pharmaceutical compositions should be stable under long term storage conditions and under the conditions of clinical use.

SUMMARY OF THE INVENTION

The subject invention provides a pharmaceutical composition comprising a protein phosphatase 2A inhibitor and monosodium glutamate.

In an embodiment of the pharmaceutical composition, the protein phosphatase 2A inhibitor has the structure

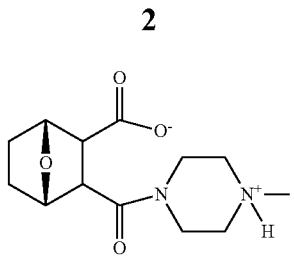

or a salt or enantiomer thereof.

The invention also provides a sealed package comprising the pharmaceutical composition of the invention.

The invention also provides a method of preparing a pharmaceutical composition for administration to a subject, comprising mixing an amount of the pharmaceutical composition of the invention with a saline solution.

The invention also provides a method of preparing a pharmaceutical composition for administration to a subject, comprising removing an amount of pharmaceutical composition from the sealed package of the invention and mixing the amount of the pharmaceutical composition with a saline solution.

The invention also provides a pharmaceutical composition produced by the above methods.

The invention also provides a method of making the pharmaceutical composition of the invention, comprising
a) adding an amount of monosodium glutamate to an amount of water to form a mixture of monosodium glutamate and water; and
b) adding an amount of a protein phosphatase 2 inhibitor to the mixture.

The invention also provides a pharmaceutical composition produced by the above method.

The invention also provides a method of treating a subject afflicted with a condition or disease amenable to treatment with a PP2A inhibitor comprising administering to the subject a pharmaceutical composition of the invention in an amount effective to treat the subject.

The invention also provides a method of treating a subject afflicted with cancer comprising administering to the subject a pharmaceutical composition of the invention in an amount effective to treat the subject.

The invention also provides a method of treating a subject afflicted with a neurodegenerative disease comprising administering to the subject a pharmaceutical composition of the invention in an amount effective to treat the subject.

The invention also provides a method of treating a subject afflicted with a disease characterized by a loss of protein function caused by a genetic abnormality associated with the disease comprising administering to the subject a therapeutically effective amount of a pharmaceutical composition of the invention.

The invention also provides methods of reducing reperfusion injury, tissue damage associated with reperfusion injury, vascular leakage associated with reperfusion injury, tissue damage due to an acute trauma, and vascular leakage due to an acute trauma, comprising administering a therapeutically effective amount of a pharmaceutical composition of the invention to a subject in need thereof.

BRIEF DESCRIPTION OF THE DRAWINGS

FIG. 1: Representative HPLC chromatogram for the formulation of 1 mg/ml LB-100 in 0.1 M monosodium glutamate, pH 10.5, after 9 months of storage at −20° C.±10° C.

DETAILED DESCRIPTION OF THE INVENTION

The subject invention provides a pharmaceutical composition comprising a protein phosphatase 2A inhibitor and monosodium glutamate.

In an embodiment of the pharmaceutical composition, the protein phosphatase 2A inhibitor has the structure

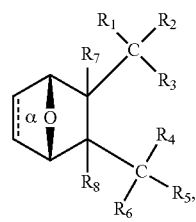

wherein
bond α is present or absent;
$R_1$ and $R_2$ is each independently H, O⁻ or $OR_9$,
where $R_9$ is H, alkyl, alkenyl, alkynyl or aryl,
or $R_1$ and $R_2$ together are =O;
$R_3$ and $R_4$ are each different, and each is OH, O⁻, SH, S⁻, $SR_9$,

[three substituent structures shown]

where X is O, S, $NR_{10}$, or $N^+R_{10}R_{10}$,
where each $R_{10}$ is independently H, alkyl, substituted $C_2$-$C_{12}$ alkyl, alkenyl, substituted $C_4$-$C_{12}$ alkenyl, alkynyl, substituted alkynyl, aryl, substituted aryl where the substituent is other than chloro when $R_1$ and $R_2$ are =O,

[two substituent structures shown]

—$CH_2CN$, —$CH_2CO_2R_{11}$, —$CH_2COR_{11}$, —$NHR_{11}$ or —$NH^+(R_{11})_2$,
where each $R_{11}$ is independently alkyl, alkenyl or alkynyl, each of which is substituted or unsubstituted, or H;
$R_5$ and $R_6$ is each independently H, OH, or $R_5$ and $R_6$ taken together are =O; and
$R_7$ and $R_8$ is each independently H, F, Cl, Br, $SO_2Ph$, $CO_2CH_3$, or $SR_{12}$,
where $R_{12}$ is H, aryl or a substituted or unsubstituted alkyl, alkenyl or alkynyl,
or a salt, enantiomer or zwitterion of the compound.

In an embodiment of the pharmaceutical composition, the protein phosphatase 2A inhibitor has the structure

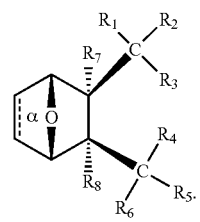

In an embodiment of the pharmaceutical composition, the protein phosphatase 2A inhibitor has the structure

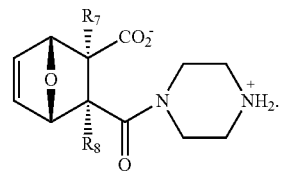

In an embodiment of the pharmaceutical composition, the protein phosphatase 2A inhibitor has the structure

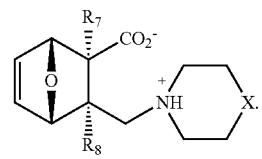

In an embodiment of the pharmaceutical composition, bond α is present.

In an embodiment of the pharmaceutical composition, bond α is absent.

In an embodiment of the pharmaceutical composition, $R_1$ and $R_2$ together are =O;
$R_3$ is O⁻ or $OR_9$,
where $R_9$ is H, methyl, ethyl or phenyl;
$R_4$ is

[three substituent structures shown]

where X is O, S, $NR_{10}$, or $N^+R_{10}R_{10}$,
where each $R_{10}$ is independently H, alkyl, substituted $C_2$-$C_{12}$ alkyl, alkenyl, substituted $C_4$-$C_{12}$ alkenyl, alkynyl, substituted alkynyl, aryl, substituted aryl where the substituent is other than chloro,

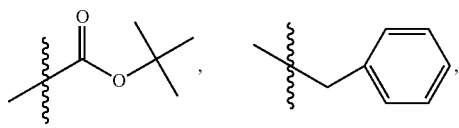

—CH$_2$CN, —CH$_2$CO$_2$R$_{11}$, —CH$_2$COR$_{11}$, —NHR$_{11}$ or —NHR$_{11}$ or —NH$^+$(R$_{11}$)$_2$, where R$_{11}$ is alkyl, alkenyl or alkynyl, each of which is substituted or unsubstituted, or H;

R$_5$ and R$_6$ taken together are =O; and

R$_7$ and R$_8$ is each independently H, F, Cl, Hr, SO$_2$Ph, CO$_2$CH$_3$, SR$_{12}$, where R$_{12}$ is a substituted or unsubstituted alkyl, alkenyl or alkynyl.

In an embodiment of the pharmaceutical composition, R$_3$ is O$^-$.

In an embodiment of the pharmaceutical composition, R$_4$ is

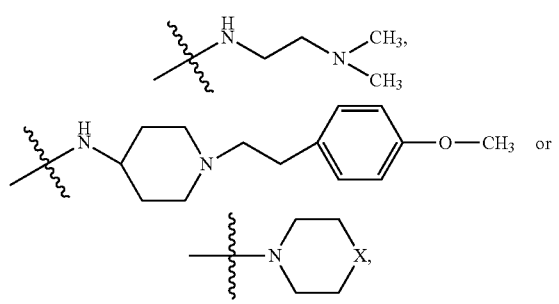

where X is O, NR$_{10}$, N$^+$R$_{10}$R$_{10}$ where each R$_{10}$ is independently H, alkyl, substituted C$_2$-C$_{12}$ alkyl, alkenyl, substituted C$_4$-C$_{12}$ alkenyl, alkynyl, substituted alkynyl, aryl, substituted aryl where the substituent is other than chloro when R$_1$ and R$_2$ are =O,

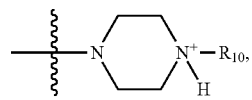

—CH$_2$CN, —CH$_2$CO$_2$R$_{11}$, —CH$_2$COR$_{11}$, —NHR$_{11}$ or —NH$^+$(R$_{11}$)$_2$, where R$_{11}$ is H or alkyl.

In an embodiment of the pharmaceutical composition, the protein phosphatase inhibitor 2A has the structure

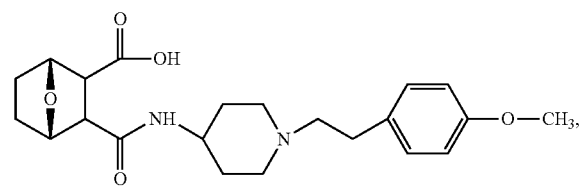

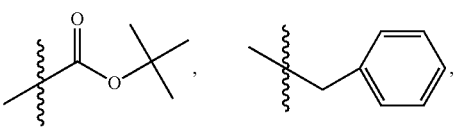

In an embodiment of the pharmaceutical composition, R$_4$ is

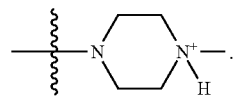

where R$_{10}$ is R$_{10}$H, alkyl, substituted C$_2$-C$_{12}$ alkyl, alkenyl, substituted C$_4$-C$_{12}$ alkenyl, alkynyl, substituted alkynyl, aryl, substituted aryl where the substituent is other than chloro when R$_1$ and R$_2$ are =O,

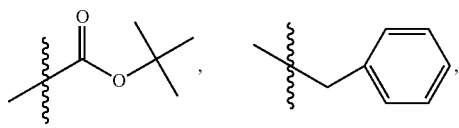

—CH$_2$CN, —CH$_2$CO$_2$R$_{11}$, —CH$_2$COR$_{11}$, —NHR$_{11}$ or —NH$^+$(R$_{11}$)$_2$, where R$_{11}$ is H or alkyl.

In an embodiment of the pharmaceutical composition, R$_4$ is

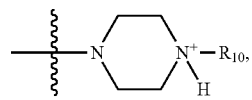

In an embodiment of the pharmaceutical composition, R$_4$ is

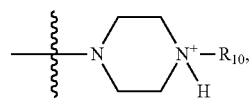

where $R_{10}$ is

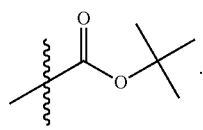 [SMILES: *C(=O)OC(C)(C)C]

In an embodiment of the pharmaceutical composition, $R_4$ is

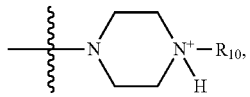

where $R_{10}$ is

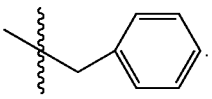 [SMILES: *Cc1ccccc1]

In an embodiment of the pharmaceutical composition, $R_4$ is

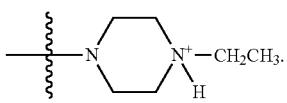

In an embodiment of the pharmaceutical composition, $R_4$ is

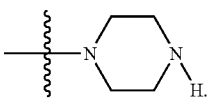

In an embodiment of the pharmaceutical composition, $R_5$ and $R_6$ together are =O.

In an embodiment of the pharmaceutical composition, $R_7$ and $R_8$ are each H.

In an embodiment of the pharmaceutical composition, the protein phosphatase 2A inhibitor has the structure

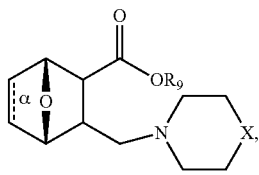

wherein bond α is present or absent; $R_9$ is present or absent and when present is H, $C_1$-$C_{10}$ alkyl, $C_2$-$C_{10}$ alkenyl or phenyl; and X is O, S, $NR_{10}$ or $N^+R_{10}R_{10}$, where each $R_{10}$ is independently H, alkyl, substituted $C_2$-$C_{12}$ alkyl, alkenyl, substituted $C_4$-$C_{12}$ alkenyl, alkynyl, substituted alkynyl, aryl, substituted aryl where the substituent is other than chloro,

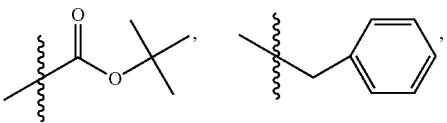

—$CH_2CO_2R_{11}$, —$CH_2COR_{11}$, —$CH_2CN$, or —$CH_2CH_2R_{16}$, where $R_{11}$ is H or alkyl, and where $R_{16}$ is any substitutent that is a precursor to an aziridinyl intermediate, or a salt, zwitterion or enantiomer of the compound.

In an embodiment of the pharmaceutical composition, the protein phosphatase 2A inhibitor has the structure

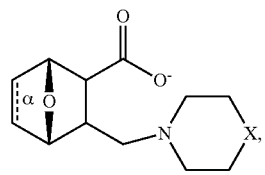

wherein,
bond α is present or absent;
X is O, S, $NR_{10}$ or $N^+R_{10}R_{10}$,
where each $R_{10}$ is independently H, alkyl, substituted $C_2$-$C_{12}$ alkyl, alkenyl, substituted $C_4$-$C_{12}$ alkenyl, alkynyl, substituted alkynyl, aryl, substituted aryl where the substituent is other than chloro,

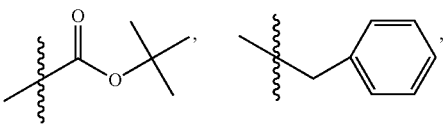

—$CH_2CO_2R_{11}$, —$CH_2COR_{11}$, —$CH_2CN$, or —$CH_2CH_2R_{16}$, where $R_{11}$ is H or alkyl, and where $R_{16}$ is any substitutent that is a aziridinyl intermediate, or a salt, zwitterion or enantiomer of the compound.

In an embodiment of the pharmaceutical composition, X is O or $NH^+R_{10}$,
where $R_{10}$ is H, alkyl, substituted $C_2$-$C_{12}$ alkyl, alkenyl, substituted $C_4$-$C_{12}$ alkenyl, alkynyl, substituted alkynyl, aryl, substituted aryl where the substituent is other than chloro,

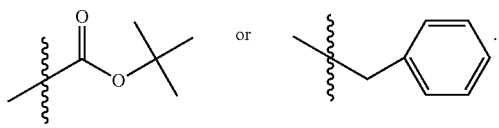

In an embodiment of the pharmaceutical composition, X is —$CH_2CH_2R_{16}$, where $R_{16}$ is any substitutent that is a precursor to an aziridinyl intermediate.

In an embodiment of the pharmaceutical composition, X is O.

In an embodiment of the pharmaceutical composition, X is $NH^+R_{10}$, where $R_{10}$ H, alkyl, substituted $C_2$-$C_{12}$ alkyl, alkenyl, substituted $C_4$-$C_{12}$ alkenyl, alkynyl, substituted alkynyl, aryl, substituted aryl where the substituent is other than chloro,

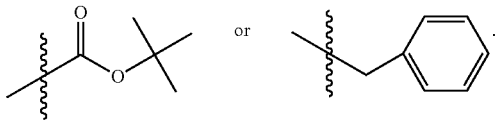

In an embodiment of the pharmaceutical composition, $R_{10}$ is methyl.

In an embodiment of the pharmaceutical composition, $R_{10}$ is

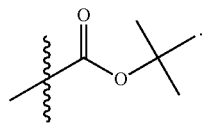

In an embodiment of the pharmaceutical composition, $R_{10}$ is

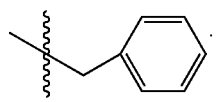

In an embodiment of the pharmaceutical composition, $R_{10}$ is ethyl.

In an embodiment of the pharmaceutical composition, $R_{10}$ is absent.

In an embodiment of the pharmaceutical composition, the protein phosphatase 2A inhibitor has the structure

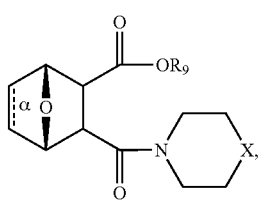

wherein bond α is present or absent;

$R_9$ is present or absent and when present is H, alkyl, alkenyl, alkynyl or phenyl; and X is O, $NR_{10}$, or $N^+R_{10}R_{10}$, where each $R_{10}$ is independently H, alkyl, substituted $C_2$-$C_{12}$ alkyl, alkenyl, substituted $C_4$-$C_{12}$ alkenyl, alkynyl, substituted alkynyl, aryl, substituted aryl where the substituent is other than chloro,

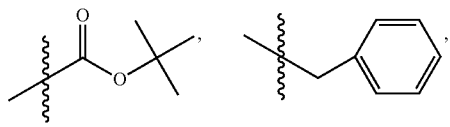

—$CH_2CN$, —$CH_2CO_2R_{12}$, or —$CH_2COR_{12}$, where $R_{12}$ is H or alkyl, or a salt, zwitterion, or enantiomer of the compound.

In an embodiment of the pharmaceutical composition, the protein phosphatase 2A inhibitor has the structure

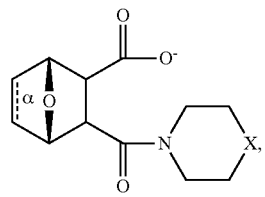

wherein bond α is present or absent;

X is O or $NH^+R_{10}$, where $R_{10}$ is H, alkyl, substituted $C_2$-$C_{12}$ alkyl, alkenyl, substituted $C_4$-$C_{12}$ alkenyl, alkynyl, substituted alkynyl, aryl, substituted aryl where the substituent is other than chloro,

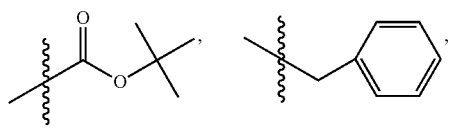

—$CH_2CN$, —$CH_2CO_2R_{12}$, or —$CH_2COR_{12}$, where $R_{12}$ is H or alkyl.

In an embodiment of the pharmaceutical composition, bond α is present.

In an embodiment of the pharmaceutical composition, bond α is absent.

In an embodiment of the pharmaceutical composition, the protein phosphatase 2A inhibitor has the structure

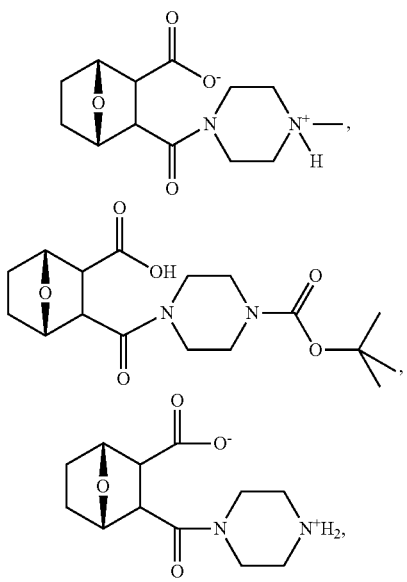

-continued

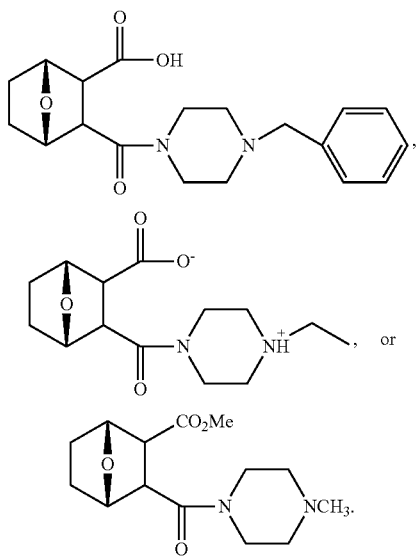

In an embodiment of the pharmaceutical composition, the protein phosphatase 2A inhibitor has the structure

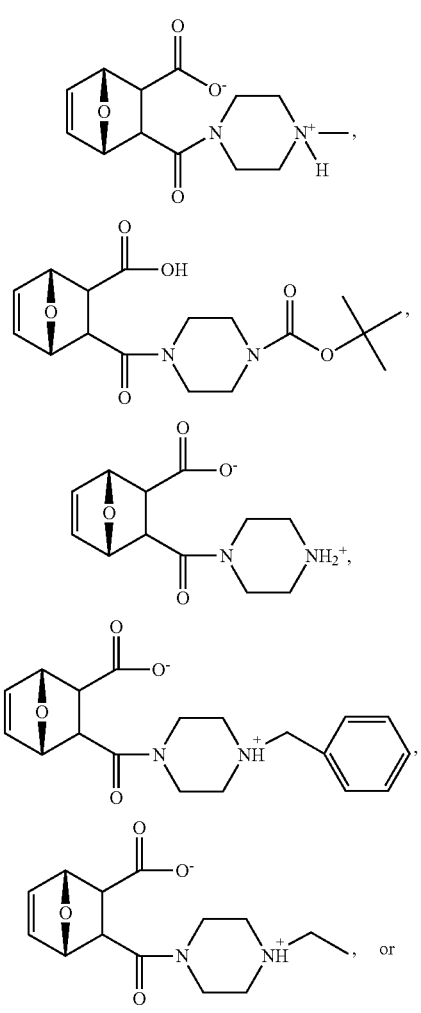

-continued

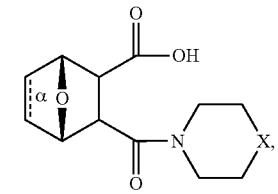

In an embodiment of the pharmaceutical composition, the protein phosphatase 2A inhibitor has the structure

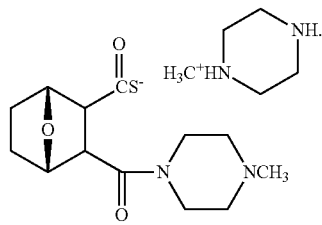

wherein
bond α is present or absent; X is $NH^+R_{10}$,
  where $R_{10}$ is present or absent and when present $R_{10}$ is alkyl, substituted C2-C12 alkyl, alkenyl, substituted C4-C12 alkenyl,

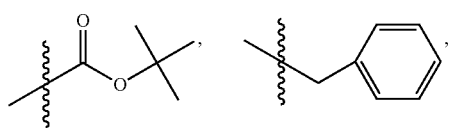

—$CH_2CN$, —$CH_2CO_2R_{12}$, or —$CH_2COR_{12}$, where $R_{12}$ is H or alkyl.

In an embodiment of the pharmaceutical composition, the protein phosphatase 2A inhibitor has the structure

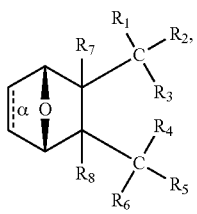

In an embodiment of the pharmaceutical composition, the protein phosphatase 2A inhibitor has the structure wherein
bond α is present or absent;
$R_1$ and $R_2$ is each independently H, $O^-$ or $OR_9$,
  where $R_9$ is H, alkyl, substituted alkyl, alkenyl, alkynyl or aryl, or $R_1$ and $R_2$ together are $=O$;
$R_3$ and $R_4$ are each different, and each is $O(CH_2)_{1-6}R_9$ or $OR_{10}$, or

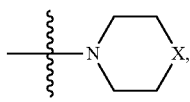

where X is O, S, $NR_{11}$, or $N^+R_{11}R_{11}$,
where each $R_{11}$ is independently H, alkyl, hydroxyalkyl, substituted $C_2$-$C_{12}$ alkyl, alkenyl, substituted $C_4$-$C_{12}$ alkenyl, alkynyl, substituted alkynyl, aryl, substituted aryl where the substituent is other than chloro when $R_1$ and $R_2$ are $=O$,

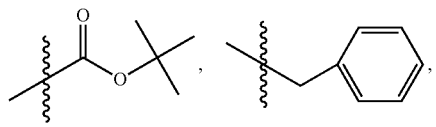

—$CH_2CN$, —$CH_2CO_2R_{12}$, —$CH_2COR_{12}$, —$NHR_{12}$ or —$NH^+(R_{12})_2$,
where each $R_{12}$ is independently alkyl, alkenyl or alkynyl, each of which is substituted or unsubstituted, or H;
where $R_{10}$ is substituted alkyl, substituted alkenyl, substituted alkynyl, or substituted aryl,
or $R_3$ and $R_4$ are each different and each is OH or

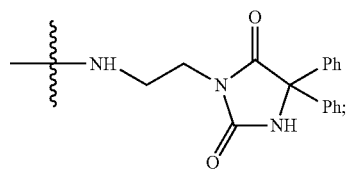 [SMILES: *NCCN1C(=O)NC(c2ccccc2)(c2ccccc2)C1=O]

$R_5$ and $R_6$ is each independently H, OH, or $R_5$ and $R_6$ taken together are $=O$; and
$R_7$ and $R_8$ is each independently H, F, Cl, Br, $SO_2Ph$, $CO_2CH_3$, or $SR_{13}$,
where $R_{13}$ is H, aryl or a substituted or unsubstituted alkyl, alkenyl or alkynyl,
or a salt, enantiomer or zwitterion of the compound.

In an embodiment of the pharmaceutical composition, the protein phosphatase 2A inhibitor has the structure

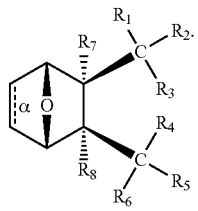

In an embodiment of the pharmaceutical composition, bond α is present.
In an embodiment of the pharmaceutical composition, bond α is absent.
In an embodiment of the pharmaceutical composition, $R_3$ is $OR_9$ or $O(CH_2)_{1-6}R_{10}$,
where $R_9$ is aryl or substituted ethyl;
where $R_{10}$ is substituted phenyl, wherein the substituent is in the para position;

$R_4$ is

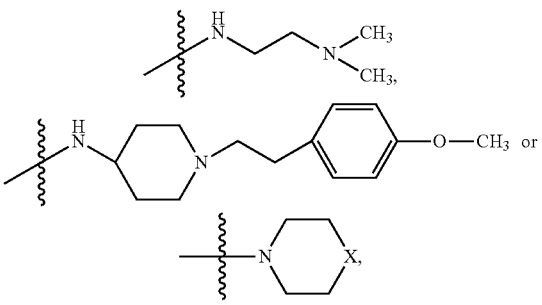

where X is O, S, $NR_{11}$, or $N^+R_{11}R_{11}$,
where each $R_{11}$ is independently H, alkyl, hydroxyalkyl, substituted $C_2$-$C_{12}$ alkyl, alkenyl, substituted $C_4$-$C_{12}$ alkenyl, alkynyl, substituted alkynyl, aryl, substituted aryl where the substituent is other than chloro,

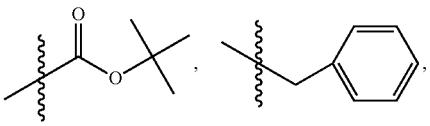

—$CH_2CN$, —$CH_2CO_2R_{12}$, —$CH_3COR_{12}$, —$NHR_{12}$ or —$NH^+(R_{12})_2$,
where $R_{12}$ is alkyl, alkenyl or alkynyl, each of which is substituted or unsubstituted, or H;
or where $R_3$ is OH and $R_4$ is

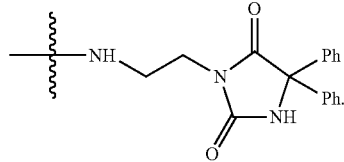 [SMILES: *NCCN1C(=O)NC(c2ccccc2)(c2ccccc2)C1=O]

In an embodiment of the pharmaceutical composition, $R_4$ is

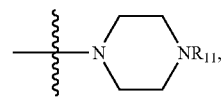

where $R_{11}$ is alkyl or hydroxylalkyl
or $R_4$ is

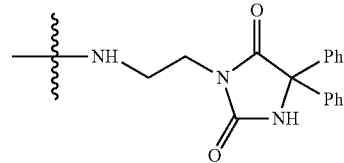 [SMILES: *NCCN1C(=O)NC(c2ccccc2)(c2ccccc2)C1=O]

when $R_3$ is OH.
In an embodiment of the pharmaceutical composition, $R_1$ and $R_2$ together are $=O$;
$R_3$ is $OR_9$ or $OR_{10}$ or $O(CH_2)_{1-2}R_9$,
where $R_9$ is aryl or substituted ethyl;
where $R_{10}$ is substituted phenyl, wherein the substituent is in the para position;

or $R_3$ is OH and $R_4$ is

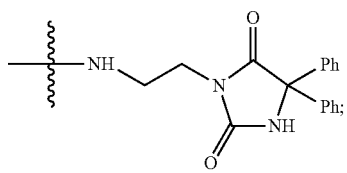 [SMILES: *NCCN1C(=O)NC(c2ccccc2)(c2ccccc2)C1=O]

$R_4$ is

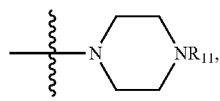

where $R_{11}$ is alkyl or hydroxyl alkyl;
$R_5$ and $R_6$ together are =O; and
$R_7$ and $R_8$ are each independently H.
In an embodiment of the pharmaceutical composition,
$R_1$ and $R_2$ together are =O;
$R_3$ is OH, O(CH$_2$)R$_9$, or OR$_{10}$,
where $R_9$ is phenyl;
where $R_{10}$ is CH$_2$CCl$_3$,

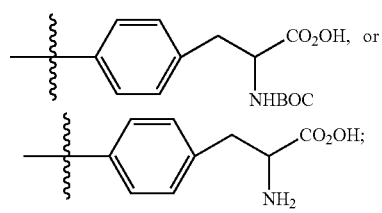

$R_4$ is

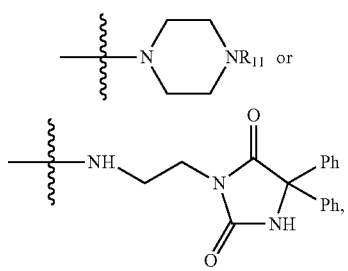

where $R_{11}$ is CH$_3$ or CH$_3$CH$_2$OH;
$R_5$ and $R_6$ together are =O; and
$R_7$ and $R_8$ are each independently H.
In an embodiment of the pharmaceutical composition, $R_3$ is OR$_{10}$, where $R_{10}$ is (CH$_2$)$_{1-6}$ (CHNHBOC)CO$_2$H, (CH$_2$)$_{1-6}$ (CHNH$_2$)CO$_2$H, or (CH$_2$)$_{1-6}$CCl$_3$.
In an embodiment of the pharmaceutical composition, $R_{10}$ is CH$_2$ (CHNHBOC) CO$_2$H.
In an embodiment of the pharmaceutical composition, $R_{10}$ is CH$_2$(CHNH$_2$)CO$_2$H.
In an embodiment of the pharmaceutical composition, $R_{10}$ is CH$_2$CCl$_3$.
In an embodiment of the pharmaceutical composition, $R_3$ is O(CH$_2$)$_{1-6}$R$_9$ where $R_9$ is phenyl.

In an embodiment of the pharmaceutical composition, $R_3$ is O(CH$_2$)R$_9$ where $R_9$ is phenyl.
In an embodiment of the pharmaceutical composition, $R_3$ is OH and $R_4$ is

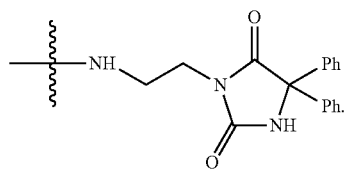 [SMILES: *NCCN1C(=O)NC(c2ccccc2)(c2ccccc2)C1=O]

In an embodiment of the pharmaceutical composition, $R_4$ is

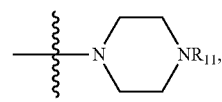

wherein $R_{11}$ is hydroxyalkyl.
In an embodiment of the pharmaceutical composition, $R_{11}$ is —CH$_2$CH$_2$OH.
In an embodiment of the pharmaceutical composition, $R_4$ is

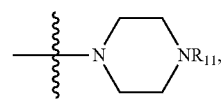

wherein $R_{11}$ is alkyl.
In an embodiment of the pharmaceutical composition, $R_{11}$ is —CH$_3$.
In an embodiment of the pharmaceutical composition, $R_4$ is

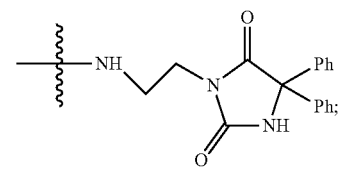 [SMILES: *NCCN1C(=O)NC(c2ccccc2)(c2ccccc2)C1=O]

In an embodiment of the pharmaceutical composition, the protein phosphatase 2A inhibitor has the structure

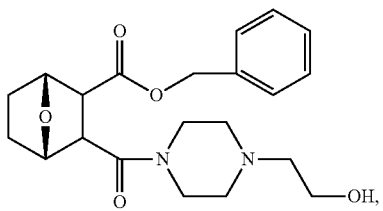

-continued

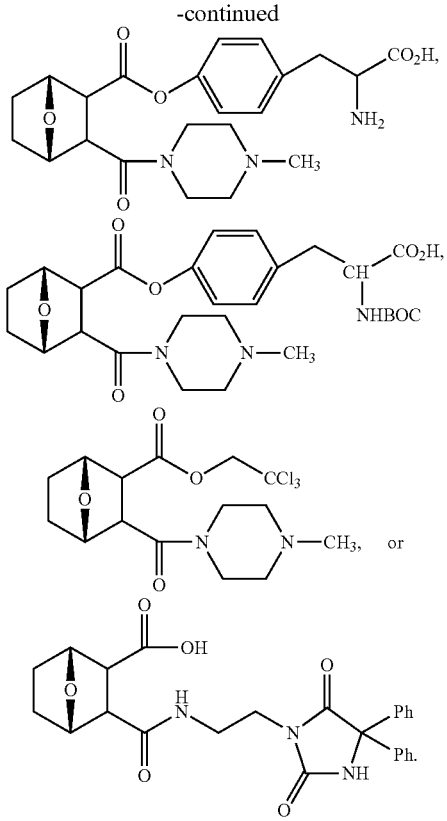

In an embodiment of the pharmaceutical composition, the protein phosphatase 2A inhibitor has the structure

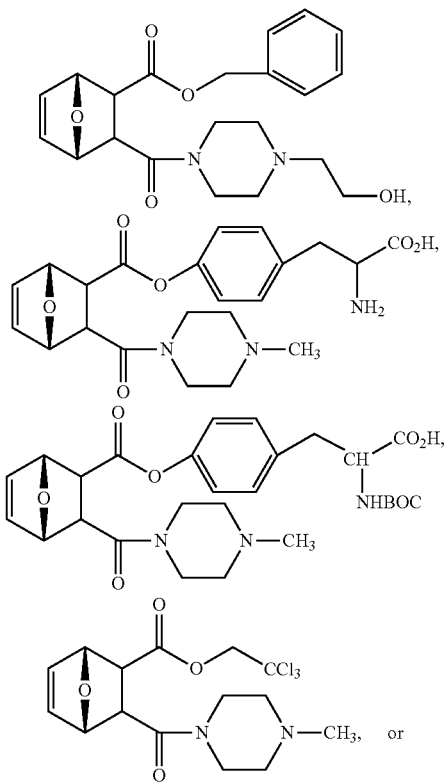

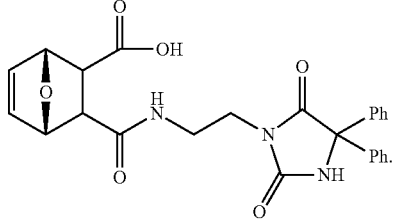

In an embodiment of the pharmaceutical composition, the protein phosphatase 2A inhibitor has the structure

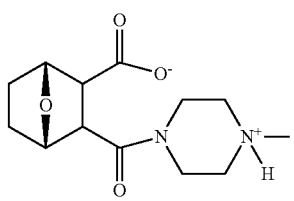 [SMILES: C[NH+]1CCN(C(=O)C2C(C(=O)[O-])[C@H]3CC[C@@H]2O3)CC1]

or a salt or enantiomer thereof.

In an embodiment of the pharmaceutical composition, the pharmaceutical composition further comprises water.

In an embodiment, the pH of the pharmaceutical composition is 10-11.

In an embodiment, the pH of the pharmaceutical composition is 10.4-10.6

In an embodiment, the pH of the pharmaceutical composition is 10.5.

In an embodiment of the pharmaceutical composition, the protein phosphatase 2A inhibitor is present in the pharmaceutical composition at a concentration of 1.0 mg/mL.

In an embodiment of the pharmaceutical composition, the monosodium glutamate is present in the pharmaceutical composition at a concentration of 0.1 M.

The invention also provides a sealed package comprising pharmaceutical composition of the invention.

In an embodiment, the sealed package is a vial.

In an embodiment, the sealed package comprises 10 mL of the pharmaceutical composition.

The invention also provides a method of preparing a pharmaceutical composition for administration to a subject, comprising mixing an amount of the pharmaceutical composition of the invention with a saline solution.

The invention also provides a method of preparing a pharmaceutical composition for administration to a subject, comprising removing an amount of pharmaceutical composition from the sealed package of the invention and mixing the amount of the pharmaceutical composition with a saline solution.

In an embodiment of the methods, the amount of the saline solution is 50 mL.

In an embodiment of the methods, the saline solution contains an anti-cancer cancer agent which is not LB-100.

In an embodiment of the methods, the saline solution contains a pharmaceutically acceptable carrier.

The invention also provides a pharmaceutical composition produced by the above methods.

The invention also provides a method of making the pharmaceutical composition of the invention, comprising (a) adding an amount of monosodium glutamate to an amount of water to form a mixture of monosodium glutamate and water, and (b) adding an amount of a protein phosphatase 2 inhibitor to the mixture.

In an embodiment, the method further comprises a step of adjusting the pH of the mixture after step (a), a step or adjusting the pH of the mixture after step (b), or a step of adjusting the pH of the mixture after step (a) and a step of adjusting the pH of the mixture after step (b), wherein the pH of the mixture is adjusted to a pH range of 10-11 in each pH adjusting step.

In an embodiment, the pH of the mixture is adjusted to a pH range of 10.4-10.6 in each pH adjusting step.

In an embodiment, the pH of the mixture is adjusted to 10.5 in the final pH adjustment step.

In an embodiment, the pH of the mixture is adjusted with one or both of sodium hydroxide and hydrochloric acid.

In an embodiment, the methods of making the pharmaceutical composition of the invention further comprise a final step of sterile filtering the mixture.

The invention also provides a pharmaceutical composition produced by any of the above methods.

The invention also provides a method of treating a subject afflicted with a condition or disease amenable to treatment with a PP2A inhibitor comprising administering to the subject a pharmaceutical composition of the invention in an amount effective to treat the subject.

The invention also provides a method of treating a subject afflicted with cancer comprising administering to the subject a pharmaceutical composition of the invention in an amount effective to treat the subject.

In an embodiment, the cancer is selected from acute lymphocytic leukemia, adenocarcinoma of the lung, adrenocortical cancer, bladder cancer, breast cancer, cervical cancer, chronic myelocytic leukemia, colon cancer, esophageal, gallbladder, glioblastoma multiforme, head and neck cancer, Hodgkin lymphoma, non-Hodgkin lymphoma, large cell lung cancer, liver cancer, medulloblastoma, melanoma, neuroblastoma, osteosarcoma, ovary adenocarcinoma, pancreatic cancer, promyelocytic leukemia, prostate carcinoma, rectal cancer, renal cancer, soft tissue sarcoma, small cell lung cancer, stomach cancer, thyroid cancer and throat cancer.

In an embodiment, cells of the cancer overexpress N-CoR.

In an embodiment, cells of the cancer do not overexpress N-CoR.

In an embodiment, cells of the cancer overexpress TCTP.

In an embodiment, the method further comprises administering to the subject an anti-cancer agent in an amount such that the amount of the pharmaceutical composition and the amount of anti-cancer agent together are effective to treat the subject.

In an embodiment, the anti-cancer agent is a chemotherapeutic agent, a DNA intercalating agent, a spindle poison or a DNA damaging agent.

In an embodiment, the anti-cancer agent is docetaxel.

In an embodiment, the method further comprises administering to the subject an amount of ionizing radiation such that the amount of the pharmaceutical composition and the amount of the ionizing radiation together are effective to treat the subject.

In an embodiment, the method further comprises administering a retinoid receptor ligand in an amount such that the amount of the pharmaceutical composition and the amount of the retinoid receptor ligand together are effective to treat the subject. In an embodiment, the retinoid receptor ligand may be a retinoid, such as a retinoic acid, e.g. cis retinoic acid or trans retinoic acid. The cis retinoic acid may be 13-cis retinoic acid and the trans retinoic acid may be all-trans retinoic acid. In an embodiment, the retinoic acid is all-trans retinoic acid (ATRA).

Retinoid receptor ligands used in the method of the invention include vitamin A (retinol) and all its natural and synthetic derivatives (retinoids).

In an embodiment, the method further comprises administering a histone deacetylase ligand in an amount such that the amount the pharmaceutical composition and the amount of the histone deacetylase ligand together are effective to treat the subject.

In an embodiment, the histone deacetylase ligand may be an inhibitor, e.g. the histone deacetylase inhibitor HDAC-3 (histone deacetylase-3). The histone deacetylase ligand may also be selected from the group consisting of 2-amino-8-oxo-9,10-epoxy-decanoyl, 3-(4-aroyl-1H-pyrrol-2-yl)-N-hydroxy-2-propenamide, APHA Compound 8, apicidin, arginine butyrate, butyric acid, depsipeptide, depudecin, HDAC-3, m-carboxycinnamic acid bis-hydroxamide, N-(2-aminophenyl)-4-[N-(pyridin-3-ylmethoxycarbonyl)aminomethyl]benzamide, MS 275, oxamfiatin, phenylbutyrate, pyroxamide, scriptaid, sirtinol, sodium butyrate, suberic bishydroxamic acid, suberoylanilide hydroxamic acid, trichostatin A, trapoxin A, trapoxin B and valproic acid. In another embodiment of the invention, the inhibitor is valproic acid.

In an embodiment, the method further comprises administering both a retinoid receptor ligand and a histone deacetylase ligand each in an amount such that the amount of the pharmaceutical composition, the amount of the histone deacetylase ligand and the amount of the retinoid receptor ligand together are effective to treat the subject.

The invention also provides a method of treating a subject afflicted with a neurodegenerative disease comprising administering to the subject a pharmaceutical composition of the invention in an amount effective to treat the subject.

In an embodiment, the neurodegenerative disease is Alzheimer's disease, Mild Cognitive Impairment, Parkinsons Disease, Frontotemporal Dementia, Dementia, or Lewy Body Dementia.

In an embodiment, the method further comprises administering to the subject an NMDA receptor antagonist, an acetylcholinesterase inhibitor, an anti-amyloid antibody, a 5-HT6 antagonist, a gamma secretase inhibitor, a beta secretase inhibitor, an inhibitor of aggregation of amyloid-$\beta$ peptide, or a tau aggregation inhibitor.

The invention also provides a method of treating a subject afflicted with a disease characterized by a loss of protein function caused by a genetic abnormality associated with the disease comprising administering to the subject a therapeutically effective amount of a pharmaceutical composition of the invention.

In an embodiment, the disease is selected from Gaucher's disease, von Hippel-Lindau disease, cystic fibrosis, Phenylketonuria, Fabry disease, Tay-Sachs disease, Pompe disease, Neimann-Pick disease (Type A, B and C), Marfan syndrome, Hemophilia A & B, retinitis pigmentosa, Neurofibromatosis Type 2, pheochromocytoma, paraganglioma, Multiple Endocrine Neoplasia Type 1, Familial Hypercholesterolemia, Hurler's disease, Hunter syndrome, Sanfilippo syndrome, Morquio syndrome, Maroteaux-Lamy syndrome, Sly syndrome, Sandhoff's disease, Fucosidosis, alpha-mannosidosis, beta-mannosidosis, aspartylglucosaminuria, Sialidosis, Inclusion-cell (I-cell) disease, Pseudo-Hurler polydystrophy, Krabbe's disease, Metachromatic leukodystrophy, multiple sulfatase deficiency, Wolmen's disease, Cholesteryl ester storage disease, Late onset GAA deficiency, Danon's disease, Neutropenia, X-linked hyper IgM syndrome, X-linked agammaglobulinemia, X-linked lymphoproliferative disease, Severe Combined Immunodeficiency, Noonan syndrome, juvenile myelomonocytic leukemia, Basal cell carcinoma, STAT1 deficiency, Alzheimer's disease, Parkinson's disease, Huntington's disease, TTR Amyloid Polyneuropathy, Ataxia Telangiectasia, Creutzfeldt-Jakob disease, Type II diabetes and Hereditary Transthyretin (TTR) amyloidosis.

In an embodiment, the method further comprises administering to the subject an amount of a histone deacetylase inhibitor such that the amount of the pharmaceutical composition and the amount of histone deacetylase inhibitor together are effective to treat the subject.

The invention also provides a method of reducing reperfusion injury in a subject comprising administering to the subject a therapeutically effective amount of a pharmaceutical composition of the invention.

The invention also provides a method of reducing tissue damage associated with reperfusion injury in a subject comprising administering to the subject a therapeutically effective amount of a pharmaceutical composition of the invention.

In an embodiment, the subject has suffered an ischemia.

In an embodiment, the ischemia is caused by a myocardial infarction, stroke, or sepsis.

In an embodiment, the tissue is myocardial tissue, brain tissue, or endothelial tissue.

The invention also provides a method of reducing vascular leakage associated with reperfusion injury in a subject suffering from sepsis comprising administering to the subject a therapeutically effective amount of a pharmaceutical composition of the invention.

The invention also provides a method of reducing tissue damage due to an acute trauma in a subject comprising administering to the subject a therapeutically effective amount of a pharmaceutical composition of the invention.

The invention also provides a method of reducing vascular leakage due to an acute trauma in a subject, comprising administering to the subject a therapeutically effective amount of a pharmaceutical composition of the invention.

In an embodiment of the above methods, the pharmaceutical composition is administered intravenously.

In an embodiment of the above methods, the amount of LB-100 administered is 1 mg to 12 mg per dose.

The invention also provides a pharmaceutical composition as described herein for use in treating a subject afflicted with a condition or disease amenable to treatment with a PP2A inhibitor.

The invention also provides a pharmaceutical composition as described herein for use in treating a subject afflicted with cancer.

In an embodiment, the cancer is selected from acute lymphocytic leukemia, adenocarcinoma of the lung, adrenocortical cancer, bladder cancer, breast cancer, cervical cancer, chronic myelocytic leukemia, colon cancer, esophageal, gallbladder, glioblastoma multiforme, head and neck cancer, Hodgkin lymphoma, non-Hodgkin lymphoma, large cell lung cancer, liver cancer, medulloblastoma, melanoma, neuroblastoma, osteosarcoma, ovary adenocarcinoma, pancreatic cancer, promylocytic leukemia, prostate carcinoma, rectal cancer, renal cancer, soft tissue sarcoma, small cell lung cancer, stomach cancer, thyroid cancer and throat cancer.

The invention also provides a pharmaceutical composition as described for use treat a subject afflicted with neurodegenerative disease.

In an embodiment, the neurodegenerative disease is Alzheimer's disease, Mild Cognitive Impairment, Parkinsons Disease, Frontotemporal Dementia, Dementia, or Lewy Body Dementia.

The invention also provides a pharmaceutical composition as described herein for use in treating a subject afflicted with a disease characterized by a loss of protein function caused by a genetic abnormality associated with the disease.

In an embodiment, the disease is selected from Gaucher's disease, von Hippel-Lindau disease, cystic fibrosis, Phenylketonuria, Fabry disease, Tay-Sachs disease, Pompe disease, Neimann-Pick disease (Type A, B and C), Marfan syndrome, Hemophilia A & B, retinitis pigmentosa, Neurofibromatosis Type 2, pheochromocytoma, paraganglioma, Multiple Endocrine Neoplasia Type 1, Familial Hypercholesterolemia, Hurler's disease, Hunter syndrome, Sanfilippo syndrome, Morquio syndrome, Maroteaux-Lamy syndrome, Sly syndrome, Sandhoff's disease, Fucosidosis, alpha-mannosidosis, beta-mannosidosis, aspartylglucosaminuria, Sialidosis, Inclusion-cell (I-cell) disease, Pseudo-Hurler polydystrophy, Krabbe's disease, Metachromatic leukodystrophy, multiple sulfatase deficiency, Wolmen's disease, Cholesteryl ester storage disease, Late onset GAA deficiency, Danon's disease, Neutropenia, X-linked hyper IgM syndrome, X-linked agammaglobulinemia, X-linked lymphoproliferative disease, Severe Combined Immunodeficiency, Noonan syndrome, juvenile myelomonocytic leukemia, Basal cell carcinoma, STAT1 deficiency, Alzheimer's disease, Parkinson's disease, Huntington's disease, TTR Amyloid Polyneuropathy, Ataxia Telangiectasia, Creutzfeldt-Jakob disease, Type II diabetes and Hereditary Transthyretin (TTR) amyloidosis.

The invention also provides a pharmaceutical composition as described herein for use in reducing reperfusion injury.

The invention also provides a pharmaceutical composition as described herein for use in reducing tissue damage associated with reperfusion injury.

The invention also provides a pharmaceutical composition as described herein for use in reducing vascular leakage associated with reperfusion injury in a subject suffering from sepsis.

The invention also provides a pharmaceutical composition as described herein for use in reducing tissue damage due to an acute trauma.

The invention also provides a pharmaceutical composition as described herein for use in reducing vascular leakage due to an acute trauma.

The subject invention also provides the use of the pharmaceutical composition for the manufacture of a medicament for treating a subject afflicted with a condition or disease amenable to treatment with a PP2A inhibitor.

The subject invention also provides the use of the pharmaceutical composition for the manufacture of a medicament for treating a subject afflicted with cancer.

In an embodiment, the cancer is selected from acute lymphocytic leukemia, adenocarcinoma of the lung, adrenocortical cancer, bladder cancer, breast cancer, cervical cancer, chronic myelocytic leukemia, colon cancer, esophageal, gallbladder, glioblastoma multiforme, head and neck cancer, Hodgkin lymphoma, non-Hodgkin lymphoma, large cell lung cancer, liver cancer, medulloblastoma, melanoma, neuroblastoma, osteosarcoma, ovary adenocarcinoma, pancreatic cancer, promylocytic leukemia, prostate carcinoma, rectal cancer, renal cancer, soft tissue sarcoma, small cell lung cancer, stomach cancer, thyroid cancer and throat cancer.

The subject invention also provides the use of the pharmaceutical composition for the manufacture of a medicament for treating a subject afflicted with a neurodegenerative disease.

In an embodiment, the neurodegenerative disease is Alzheimer's sass, Mild Cognitive. Parkinsons Disease, Frontotemporal Dementia, Dementia, or Lewy Body Dementia.

The subject invention also provides the use of the pharmaceutical composition for the manufacture of a medicament for treating a subject afflicted with a disease characterized by a loss of protein function caused by a genetic abnormality associated with the disease.

In an embodiment, the disease is selected from Gaucher's disease, von Hippel-Lindau disease, cystic fibrosis, Phenylketonuria, Fabry disease, Tay-Sachs disease, Pompe disease, Neimann-Pick disease (Type A, B and C), Marfan syndrome, Hemophilia A & B, retinitis pigmentosa, Neurofibromatosis Type 2, pheochromocytoma, paraganglioma, Multiple Endocrine Neoplasia Type 1, Familial Hypercholesterolemia, Hurler's disease, Hunter syndrome, Sanfilippo syndrome, Morquio syndrome, Maroteaux-Lamy syndrome, Sly syndrome, Sandhoff's disease, Fucosidosis, alpha-mannosidosis, beta-mannosidosis, aspartylglucosaminuria, Sialidosis, Inclusion-cell (I-cell) disease, Pseudo-Hurler polydystrophy, Krabbe's disease, Metachromatic leukodystrophy, multiple sulfatase deficiency, Wolmen's disease, Cholesteryl ester storage disease, Late onset GAA deficiency, Danon's disease, Neutropenia, X-linked hyper IgM syndrome, X-linked agammaglobulinemia, X-linked lymphoproliferative disease, Severe Combined Immunodeficiency, Noonan syndrome, juvenile myelomonocytic leukemia, Basal cell carcinoma, STAT1 deficiency, Alzheimer's disease, Parkinson's disease, Huntington's disease, TTR Amyloid Polyneuropathy, Ataxia Telangiectasia, Creutzfeldt-Jakob disease, Type II diabetes and Hereditary Transthyretin (TTR) amyloidosis.

The subject invention also provides the use of the pharmaceutical composition for the manufacture a medicament for reducing reperfusion injury.

The subject invention also provides the use of the pharmaceutical composition for the manufacture of a medicament for reducing tissue damage associated with reperfusion injury.

The subject invention also provides the use of the pharmaceutical composition for the manufacture of a medicament for reducing reperfusion injury in a subject suffering from sepsis.

The subject invention also provides the use of the pharmaceutical composition for the manufacture of a medicament for reducing tissue damage due to an acute trauma.

The subject invention also provides the use of the pharmaceutical composition for the manufacture of a medicament for reducing vascular leakage due to an acute trauma.

In an embodiment of the methods and uses described herein, the subject is a mammal. In an embodiment, the subject is a human.

The invention further contemplates the use of prodrugs which are converted in vivo to the PP2A inhibitor compounds described herein (see, e.g., R. B. Silverman, 1992, "The Organic Chemistry of Drug Design and Drug Action", Academic Press, Chapter 8, the entire contents of which are hereby incorporated by reference). Such prodrugs can be used to alter the biodistribution (e.g., to allow compounds which would not typically enter a reactive site) or the pharmacokinetics of the compound.

The compounds described in the present invention are in racemic form or as individual enantiomers. The enantiomers can be separated using known techniques, such as those described, for example, in Pure and Applied Chemistry 69, 1469-1474, (1997) IUPAC.

The pharmaceutical compositions described herein can be used to treat any of the conditions identified as being treatable with a PP2A inhibitor in any of PCT International Application Publication Nos. WO 2008/097561, WO 2009/020565, WO 2010/014141, WO 2010/014220, WO 2010/014254, WO 2010/147612, and WO 2012/162535, and U.S. Provisional application No. 61/782,894. Similarly, the pharmaceutical compositions described herein can be used in any of the methods reciting a PP2A inhibitor and for any of the uses of PP2A inhibitors described in PCT International Application Publication Nos. WO 2008/097561, WO 2009/020565, WO 2010/014141, WO 2010/014220, WO 2010/014254, WO 2010/147612, and WO 2012/162535, and U.S. Provisional application No. 61/782,894.

For the foregoing embodiments, each embodiment disclosed herein is contemplated as being applicable to each of the other disclosed embodiments. Thus, all combinations of the various elements described herein are within the scope of the invention.

Definitions

As used herein, and unless otherwise stated, each of the following terms shall have the definition set forth below.

As used herein "LB-100" refers to the compound having the following structure:

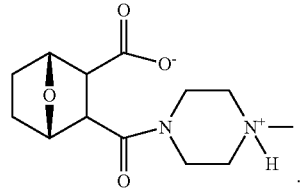 [SMILES: C[NH+]1CCN(C(=O)C2C(C(=O)[O-])[C@H]3CC[C@@H]2O3)CC1]

The chemical name of LB-100 is 3-(4methylpiperazine-carbonyl)-7-oxalobicyclo[2.2.1]heptane-2-carboxylic acid. LB-100 is also referred to as Compound 100 and LB1 in the art. Pharmaceutical compositions of the invention comprising LB-100 can contain LB-100 as a zwitterion, an enantiomer, or salt of the compound.

As used herein, "alkyl" is intended to include both branched and straight-chain saturated aliphatic hydrocarbon groups having the specified number of carbon atoms. Thus, $C_1$-$C_n$ as in "$C_1$-$C_n$ alkyl" is defined to include groups having 1, 2, . . . , n–1 or n carbons in a linear or branched arrangement, and specifically includes methyl, ethyl, propyl, butyl, pentyl, hexyl, and so on. An embodiment can be $C_1$-$C_{12}$ alkyl, "Alkoxy" represents an alkyl group as described above attached through an oxygen bridge.

The term "alkenyl" refers to a non-aromatic hydrocarbon radical, straight or branched, containing at least 1 carbon to carbon double bond, and up to the maximum possible number of non-aromatic carbon-carbon double bonds may be present. Thus, $C_2$-$C_n$ alkenyl is defined to include groups having 1, 2, . . . , n–1 or n carbons. For example, "$C_2$-$C_6$ alkenyl" means an alkenyl radical having 2, 3, 4, 5, or 6 carbon atoms, and at least 1 carbon-carbon double bond, and up to, for example, 3 carbon-carbon double bonds in the case of a $C_6$ alkenyl, respectively. Alkenyl groups include ethenyl, propenyl, butenyl and cyclohexenyl. As described above with respect to alkyl, the straight, branched or cyclic portion of the alkenyl group may contain double bonds and may be substituted if a substituted alkenyl group is indicated. An embodiment can be $C_2$-$C_{12}$ alkenyl.

The term "alkynyl" refers to a hydrocarbon radical straight or branched, containing at least 1 carbon to carbon triple bond, and up to the maximum possible number of non-aromatic carbon-carbon triple bonds may be present. Thus, $C_2$-$C_n$ alkynyl is defined to include groups having 1, 2, . . . , n−1 or n carbons. For example, "$C_2$-$C_6$ alkynyl" means an alkynyl radical having 2 or 3 carbon atoms, and 1 carbon-carbon triple bond, or having 4 or 5 carbon atoms, and up to 2 carbon-carbon triple bonds, or having 6 carbon atoms, and up to 3 carbon-carbon triple bonds. Alkynyl groups include ethynyl, propynyl and butynyl. As described above with respect to alkyl, the straight or branched portion of the alkynyl group may contain triple bonds and may be substituted if a substituted alkynyl group is indicated. An embodiment can be a $C_2$-$C_n$ alkynyl.

As used herein, "aryl" is intended to mean any stable monocyclic or bicyclic carbon ring of up to 10 atoms in each ring, wherein at least one ring is aromatic. Examples of such aryl elements include phenyl, naphthyl, tetrahydro-naphthyl, indanyl, biphenyl, phenanthryl, anthryl or acenaphthyl. In cases where the aryl substituent is bicyclic and one ring is non-aromatic, it is understood that attachment is via the aromatic ring. The substituted aryls included in this invention include substitution at any suitable position with amines, substituted amines, alkylamines, hydroxys and alkylhydroxys, wherein the "alkyl" portion of the alkylamines and alkylhydroxys is a $C_2$-$C_n$ alkyl as defined hereinabove. The substituted amines may be substituted with alkyl, alkenyl, alkynyl, or aryl groups as hereinabove defined.

The alkyl, alkenyl, alkynyl, and aryl substituents may be unsubstituted or unsubstituted, unless specifically defined otherwise. For example, a ($C_1$-$C_6$) alkyl may be substituted with one or more substituents selected from OH, oxo, halogen, alkoxy, dialkylamino, or heterocyclyl, such as morpholinyl, piperidinyl, and so on.

In the compounds of the present invention, alkyl, alkenyl, and alkynyl groups can be further substituted by replacing one or more hydrogen atoms by non-hydrogen groups described herein to the extent possible. These include, but are not limited to, halo, hydroxy, mercapto, amino, carboxy, cyano and carbamoyl.

The term "substituted" as used herein means that a given structure has a substituent which can be an alkyl, alkenyl, or aryl group as defined above. The term shall be deemed to include multiple degrees of substitution by a named substitutent. Where multiple substituent moieties are disclosed or claimed, the substituted compound can be independently substituted by one or more of the disclosed or claimed substituent moieties, singly or plurally. By independently substituted, it is meant that the (two or more) substituents can be the same or different.

It is understood that substituents and substitution patterns on the compounds of the instant invention can be selected by one of ordinary skill in the art to provide compounds that are chemically stable and that can be readily synthesized by techniques known in the art, as well as those methods set forth below, from readily available starting materials. If a substituent is itself substituted with more than one group, it is understood that these multiple groups may be on the same carbon or on different carbons, so long as a stable structure results.

As used herein, "zwitterion" means a compound that is electrically neutral but carries formal positive and negative charges on different atoms. Zwitterions are polar, have high solubility in water and have poor solubility in most organic solvents.

As used herein, a "compound" is a small molecule that does not include proteins, peptides or amino acids.

As used herein, a "mixture" is material system made up of two or more different substances. Examples of mixtures include suspensions and solutions.

As used herein, an "isolated" compound is a compound isolated from a crude reaction mixture or from a natural source following an affirmative act of isolation. The act of isolation necessarily involves separating the compound from the other components of the mixture or natural source, with some impurities, unknown side products and residual amounts of the other components permitted to remain. Purification is an example of an affirmative act of isolation.

As used herein, "anti-cancer agent" means standard cancer regimens which are currently known in the art. Examples include, but are not limited to, x-radiation, ionizing radiation, DNA damaging agents, DNA intercalating agents, microtubule stabilizing agents, microtubule destabilizing agents, spindle toxins, and chemotherapeutic agents. Further examples include cancer regimens approved by the Food and Drug Administration, which include, but are not limited to, abarelix, aldesleukin, alemtuzumab, alitertinoin, allopurinol, altretamine, amifostin, anakinra, anastrozole, arsenic trioxide, asparaginase, azacitidine, bevacizumab, bexarotene, bleomycin, bortezomib, busulfan, calusterone, capecitabine, carboplatin, carmustine, calszoxib, cetuximab, chlorambucil, cisplatin, cladribine, clofarabine, clyclophosphamide, cytarabine, dacarbazine, dactinomycin, actinomycin D, dalteparin sodium, darbepoetin alfa, dasatinib, daunorubicin, daunomycin, decitabine, denileukin, dexrazoxane, docetaxel, doxorubicin, dromostanolone propionate, exulizumab, epirubicin, epoetin alfa, erlotinib, estramustine, etoposide phosphate, etoposide, VP-16, exemestane, fentanyl citrate, filgrastim, floxuridine, fludarabine, flurouracile, fulvestrant, gefitinib, gemcitabine, gosereline acetate, histrelin acetate, hydroxyurea, ibritumomab tiuxetan, idarubicin, ifosfamide, imatinib mesylate, interferon alfa 2a, interferon alfa 2b, irinotecan, lapatinib ditosylate, lenalidomide, letrozole, leucovorin, leuprolide acetate, levamisole, lomustine, mecloretinine, megestrol acetate, melphalan, mercaptopurine, mesna, methotrexate, methoxsalen, mitomycin C, mitotane, mitoxantrone, nandrolone phenpropionate, nelarabine, nofetumomab, oprelvekin, oxaliplatin, paclitaxel, palifermin, pamidronate, panitumumab, pegademase, pegaspargase, pegfilgrastim, peginterferon alfa 2b, pemetrexed disodium, pentostatin, pipobroman, plicamycin, mithramycin, porfimer sodium, procarbazine, quinacrine, rasburicase, rituximab, sargrmostim, sorafenib, streptozocin, sunitinib, sunitinib maleate, talc, tamoxifen, temozolomide, teniposide, VM-26, testolactone, thalidomide, thioguanine, G-TG, thiotepa, topotecan, toremifene, tositumomab, trastuzumab, tretinoin ATRA, ruacil mustard, valrunicin, vinblastine, vincristine, vinorelbine, vorinostat, zoledronate, and zoledronic acid. A complete list of all FDA approved cancer drugs can be found at accessdata.fda.gov/scripts/cder/onctools/druglist.cfm.

Examples of DNA intercalating agents include, but are not limited to, doxorubicin, daunorubicin, dactinomycin. Examples of Spindle Poisons include, but are note limited to vincristine, vinblastine, taxol. DNA damaging agents include antracyclines, bleomycin, cisplatin, etoposide, temozolomide, and nitrosoureas.

As used herein, "treatment of a condition or disease" or "treating" encompasses inducing inhibition, regression, or stasis of a condition or disease.

As used herein, "inhibition" of a condition or disease in a subject means preventing or reducing the condition or disease progression and/or complication in the subject.

As used herein, a "saline solution" is a solution of NaCl in water. A saline solution can be sterile or non-sterile. A saline solution can have additional components in addition to NaCl and water, e.g. dextrose or other pharmaceutically acceptable excipient. In an embodiment, the saline solution used is "normal saline," a sterile solution of 0.9% w/v of NaCl in water.

As used herein, "administering" an agent may be performed using any of the various methods or delivery systems well known to those skilled in the art. The administering can be performed, for example, orally, parenterally, intraperitoneally, intravenously, intraarterially, transdermally, sublingually, intramuscularly, rectally, transbuccally, intranasally, liposomally, via inhalation, vaginally, intraoccularly, via local delivery, subcutaneously, intraadiposally, intraarticularly, intrathecally, into a cerebral ventricle, intraventicularly, intratumorally, into cerebral parenchyma or intraparenchchymally.

The following delivery systems, which employ a number of routinely used pharmaceutical carriers, may be used but are only representative of the many possible systems envisioned for administering compositions in accordance with the invention.

Injectable drug delivery systems include solutions, suspensions, gels, microspheres and polymeric injectables, and can comprise excipients such as solubility-altering agents (e.g., ethanol, propylene glycol and sucrose) and polymers (e.g., polycaprylactones and PLGA's).

Other injectable drug delivery systems include solutions, suspensions, gels. Oral delivery systems include tablets and capsules. These can contain excipients such as binders (e.g., hydroxypropylmethylcellulose, polyvinyl pyrilodone, other cellulosic materials and starch), diluents (e.g., lactose and other sugars, starch, dicalcium phosphate and cellulosic materials), disintegrating agents (e.g., starch polymers and cellulosic materials) and lubricating agents (e.g., stearates and talc).

Implantable systems include rods and discs, and can contain excipients such as PLGA and polycaprylactone.

Oral delivery systems include tablets and capsules. These can contain excipients such as binders (e.g., hydroxypropylmethylcellulose, polyvinyl pyrilodone, other cellulosic materials and starch), diluents (e.g., lactose and other sugars, starch, dicalcium phosphate and cellulosic materials), disintegrating agents (e.g., starch polymers and cellulosic materials) and lubricating agents (e.g., stearates and talc).

Transmucosal delivery systems include patches, tablets, suppositories, pessaries, gels and creams, and can contain excipients such as solubilizers and enhancers (e.g., propylene glycol, bile salts and amino acids), and other vehicles (e.g., polyethylene glycol, fatty acid esters and derivatives, and hydrophilic polymers such as hydroxypropylmethylcellulose and hyaluronic acid).

Dermal delivery systems include, for example, aqueous and nonaqueous gels, creams, multiple emulsions, microemulsions, liposomes, ointments, aqueous and nonaqueous solutions, lotions, aerosols, hydrocarbon bases and powders, and can contain excipients such as solubilizers, permeation enhancers (e.g., fatty acids, fatty acid esters, fatty alcohols and amino acids), and hydrophilic polymers (e.g., polycarbophil and polyvinylpyrolidone). In one embodiment, the pharmaceutically acceptable carrier is a liposome or a transdermal enhancer.

Solutions, suspensions and powders for reconstitutable delivery systems include vehicles such as suspending agents (e.g, gums, zanthans, cellulosics and sugars), humectants (e.g., sorbitol), solubilizers (e.g., ethanol, water, PEG and propylene glycol), surfactants (e.g., sodium lauryl sulfate, Spans, Tweens, and cetyl pyridine), preservatives and antioxidants (e.g., parabens, vitamins E and C, and ascorbic acid), anti-caking agents, coating agents, and chelating agents (e.g., EDTA).

As used herein, "pharmaceutically acceptable carrier" refers to a carrier or excipient that is suitable for use with humans and/or animals without undue adverse side effects (such as toxicity, irritation, and allergic response) commensurate with a reasonable benefit/risk ratio. It can be a pharmaceutically acceptable solvent, suspending agent or vehicle, for delivering the instant compounds to the subject.

The compounds used in the pharmaceutical compositions and methods of the present invention may be in a salt form. As used herein, a "salt" is a salt of the instant compounds which has been modified by making acid or base salts of the compounds. In the case of compounds used to treat an infection or disease, the salt is pharmaceutically acceptable. Examples of pharmaceutically acceptable salts include, but are not limited to, mineral or organic acid salts of basic residues such as amines; alkali or organic salts of acidic residues such as phenols. The salts can be made using an organic or inorganic acid. Such acid salts are chlorides, bromides, sulfates, nitrates, phosphates, sulfonates, formates, tartrates, maleates, malates, citrates, benzoates, salicylates, ascorbates, and the like. Phenolate salts are the alkaline earth metal salts, sodium, potassium or lithium. The term "pharmaceutically acceptable salt" in this respect, refers to the relatively non-toxic, inorganic and organic acid or base addition salts of compounds of the present invention. These salts can be prepared in situ during the final isolation and purification of the compounds of the invention, or by separately reacting a purified compound of the invention in its free base or free acid form with a suitable organic or inorganic acid or base, and isolating the salt thus formed. Representative salts include the hydrobromide, hydrochloride, sulfate, bisulfate, phosphate, nitrate, acetate, valerate, siesta, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like. (See, e.g., Berge et al. (1977) "Pharmaceutical Salts", J. Pharm. Sci. 66:1-19).

As used herein, an "amount" or "dose" of an agent measured in milligrams refers to the milligrams of agent present in a drug product, regardless of the form of the drug product.

As used herein, the term "therapeutically effective amount" or "effective amount" refers to the quantity of a component that is sufficient to yield a desired therapeutic response without undue adverse side effects (such as toxicity, irritation, or allergic response) commensurate with a reasonable benefit/risk ratio when used in the manner of this invention. The specific effective amount will vary with such factors as the particular condition being treated, the physical condition of the patient, the type of mammal being treated, the duration of the treatment, the nature of concurrent therapy (if any), and the specific formulations employed and the structure of the compounds or its derivatives.

As used herein, "cancer cell" is a cell that is characterized by uncontrolled growth and cell division and can include tumor cells. Cancer cells, which can include tumor cells, may or may not overexpress N-CoR.

As used herein, "disease characterized by a loss of protein function" is any disease wherein loss of protein function is a factor in the cause and/or progression of the disease.

As used herein, a "loss of protein function disease" or a "loss of function disease" is a "disease characterized by a loss of protein function" as defined above.

Examples of a disease characterized by a loss of protein function include, but are not limited to, Gaucher's disease, von Hippel-Lindau disease, cystic fibrosis, Phenylketonuria, Fabry disease, Tay-Sachs disease, Pompe disease, Neimann-Pick disease (Type A, B and C), Marfan syndrome, Hemophilia A & B, retinitis pigmentosa, Neurofibromatosis Type 2, pheochromocytoma, paraganglioma, Multiple Endocrine Neoplasia Type 1, Familial Hypercholesterolemia, Hurler's disease, Hunter syndrome, Sanfilippo syndrome, Morquio syndrome, Maroteaux-Lamy syndrome, Sly syndrome, Sandhoff's disease, Fucosidosis, alpha-mannosidosis, beta-mannosidosis, aspartylglucosaminuria, Sialidosis, Inclusion-cell (I-cell) disease, Pseudo-Hurler polydystrophy, Krabbe's disease, Metachromatic leukodystrophy, multiple sulfatase deficiency, Wolmen's disease, Cholesteryl ester storage disease, Late onset GAA deficiency, Danon's disease, Neutropenia, X-linked hyper IgM syndrome, X-linked agammaglobulinemia, X-linked lymphoproliferative disease, Severe Combined Immunodeficiency, Noonan syndrome, juvenile myelomonocytic leukemia, Basal cell carcinoma, STAT1 deficiency, Alzheimer's disease, Parkinson's disease, Huntington's disease, TTR Amyloid Polyneuropathy, Ataxia Telangiectasia, Creutzfeldt-Jakob disease, Type II diabetes and Hereditary transthyretin (TTR) amyloidosis.

In particular, the invention is directed to a pharmaceutical composition for treating Gaucher's disease, von Hippel-Lindau disease, pheochromocytoma, and paraganglioma.

As used herein, "overexpressing N-CoR" means that the level of the Nuclear receptor co-repressor (N-CoR) expressed in cells of the tissue tested are elevated in comparison to the levels of N-CoR as measured in normal healthy cells of the same type of tissue under analogous conditions. The nuclear receptor co-repressor (N-CoR) of the subject invention may be any molecule that binds to the ligand binding domain of the DNA-bound thyroid hormone receptor (T3R) and retinoic acid receptor (RAR). (U.S. Pat. No. 6,949,624, Liu et al.) Examples of tumors that overexpress N-CoR may include glioblastoma multiforme, breast cancer (Myers et al.), colorectal cancer (Giannini and Cavallini), small cell lung carcinoma (Waters et al.) or ovarian cancer (Havrilesky et al).

As used herein, "overexpressing TCTP" means that the level of TCTP expressed in cells of the tissued tested are elevated in comparison to the levels of TCTP as measure in normal healthy cells of the same type of tissued under analogous conditions.

As used herein, a "neurodegenerative disease" refers to a disease in which degeneration occurs of either gray or white matter, or both, of the nervous system. Thus, such a disease can be diabetic neuropathy, senile dementias, Alzheimer's disease, Mild Cognitive Impairment (MCI), dementia, Lewy Body Dementia, Frontal Temporal Lobe dementia, Parkinson's Disease, facial nerve (Bell's) palsy, glaucoma, Huntington's chorea, amyotrophic lateral sclerosis (ALS), status epilepticus, non-arteritic optic neuropathy, intervertebral disc herniation, vitamin deficiency, prion diseases such as Creutzfeldt-Jakob disease, carpal tunnel syndrome, peripheral neuropathies associated with various diseases, including but not limited to, uremia, porphyria, hypoglycemia, Sjorgren Larsson syndrome, acute sensory neuropathy, chronic ataxic neuropathy, biliary cirrhosis, primary amyloidosis, obstructive lung diseases, acromegaly, malabsorption syndromes, polycythemia vera, IgA and IgG gammapathies, complications of various drugs (e.g., metronidazole) and toxins (e.g., alcohol or organophosphates), Charcot-Marie-Tooth disease, ataxia telangectasia, Friedreich's ataxia, amyloid polyneuropathies, adrenomyeloneuropathy, Giant axonal neuropathy, Refsum's disease, Fabry's disease and lipoproteinemia.

As used herein, "tauopathies" refers to a class of neurodegenerative diseases which result from aggregation of tau protein in neurofibrillary tangles. Examples of tauopathies include, but are not limited to, Alzheimer's disease, Frontotemproal dementia (Pick's disease), Progressive Supranuclear Palsy, and Corticobasal degeneration.

Where a range is given in the specification it is understood that the range includes all integers and 0.1 units within that range, and any sub-range thereof. For example, a range of 77 to 90% is a disclosure of 77, 78, 79, 80, and 81% etc.

Where a chemical name and a chemical structure conflict, the chemical structure shall govern.

All combinations of the various elements described herein are within the scope of the invention.

This invention will be better understood by reference to the following Example, but those skilled in the art will readily appreciate that the Example is only illustrative of the invention as described more fully in the claims which follow thereafter.

Example 1. Stability Study of LB-100 in Normal Saline and Sodium Bicarbonate 1.1 Objective To determine the stability of LB-100 in normal saline and 4.2% sodium bicarbonate formulations stored at room temperature and refrigerated.

1.2 Materials and Methods 1.2.1 Formulations

LB-100 (Ash Stevens, Inc., Riverview, Mich.) was stored refrigerated and was considered stable under this storage condition.

The vehicles used in preparation of the LB-100 formulations were normal saline (0.9% sodium chloride injection USP) (Baxter, Deerfield, Ill.) and 4.2% sodium bicarbonate, prepared by diluting sodium bicarbonate injection, 8.4% (Seneca Medical, Tiffin Ohio) 2-fold with Milli-Q water.

A normal saline formulation and a 4.2% sodium bicarbonate formulation were each prepared at a target LB-100 concentration of 1.00 mg/mL as follows. Approximately 20 mg of LB-100 was weighed in a tared glass vial. Vehicle was added to obtain the desired concentration, and the preparation was mixed as necessary to achieve complete dissolution of the test article.

1.2.2 Stability Testing

A normal saline formulation and a 4.2% sodium bicarbonate formulation, each prepared at a LB-100 concentration of 1.00 mg/mL were analyzed by HPLC/MS/MS to determine LB-100 concentration on the day of preparation. Aliquots of the formulations were stored at room temperature or refrigerated for 4, 8, 24, and 48 hours before being re-analyzed to assess LB-100 stability. The mean concentration and percent of time-zero values obtained are summarized in Table 1.

TABLE 1

| Storage Condition | Storage Duration (hours) | Normal Saline Formulation (1.00 mg/mL) | 4.2% Sodium Bicarbonate Formulation (1.00 mg/mL) |
|---|---|---|---|
| | | Mean Concentration, mg/mL (% of Time-Zero) | |
| Room Temperature | 4 | 0.751 (78.7) | 0.952 (96.3) |
| | 8 | 0.579 (60.6) | 0.921 (93.2) |
| | 24 | 0.199 (20.9) | 0.797 (80.7) |
| | 48 | 0.0553 (5.80) | 0.662 (67.0) |
| Refrigerated | 4 | 0.957 (100) | 1.01 (102) |
| | 8 | 0.967 (101) | 0.974 (98.6) |
| | 24 | 0.823 (86.3) | 0.970 (98.2) |
| | 48 | 0.795 (83.4) | 0.980 (99.2) |

1.3 Results

The normal saline formulation failed to meet the acceptance criteria (mean post-storage concentration 90% of the pre-storage value) following 4, 8, 24, and 48 hours of room temperature storage (78.7%, 60.6%, 20.9%, and 5.80% of the time-zero concentration, respectively) and following 24 and 48 hours of refrigerated storage (86.3% and 83.4% of the time-zero concentration, respectively). The sodium bicarbonate formulation failed to meet the acceptance criteria following 24 and 48 hours of room temperature storage (80.7% and 67.0% of the time-zero concentration, respectively).

1.4 Conclusions

An HPLC/MS/MS method for the determination of LB-100 concentration was used to assess test article stability in a normal saline formulation and in a 4.2% sodium bicarbonate formulation, each prepared at a target test article concentration of 1.00 mg/mL. The stability assessments were conducted following 4, 8, 24, and 48 hours of room temperature or refrigerated storage. The normal saline formulation failed to meet the acceptance criteria following 4, 8, 24, and 48 hours of room temperature storage and following 24 and 48 hours of refrigerated storage. The sodium bicarbonate formulation failed to meet the acceptance criteria following 24 and 48 hours of room temperature storage.

Example 2. Stability of LB-100 in Glutamate, Triethanolamine, and Phosphate Buffers 2.1 Objective To compare the long term storage stability of LB-100 in the following formulations:
1 mg/mL LB-100 in a glutamate buffer at pH 8.5±0.1;
1 mg/mL LB-100 in a glutamate buffer at pH 10.5±0.1;
1 mg/mL LB-100 in a triethanolamine buffer at pH 7.0±0.1;
1 mg/mL LB-100 in a triethanolamine buffer at pH 9.0±0.1; and
1 mg/mL LB-100 in a phosphate buffer at pH 8.0±0.1.

2.2 Materials and Methods 2.2.1 Formulations 2.2.1.1 0.1 M Glutamate Solution 28.1 g±0.1 g of L-glutamic acid monosodium salt monohydrate was weighed and added to 1500 mL of nanopure water. The mixture was mixed until all of the salt was dissolved to form a stack solution of 0.1 M L-glutamic acid monosodium salt monohydrate.

The pH of 750 mL of the L-glutamic acid monosodium salt monohydrate stock solution was adjusted to 8.5±0.1 using 0.1 N sodium hydroxide and/or 0.1 N hydrochloric acid, as necessary.

The pH of 750 mL of the L-glutamic acid monosodium salt monohydrate stock solution was adjusted to 10.5±0.1 using 0.1 N sodium hydroxide and/or 0.1 N hydrochloric acid, as necessary.

2.2.1.2 0.1 M Triethanolamine Solution 22.4 g±0.1 g of triethanolamine was weighed an added to 1500 mL of nanopure water. The mixture was mixed to form a 0.1 M triethanolamine stock solution.

The pH of 750 ml of the triethanolamine stock solution was adjusted to 7.0±0.1 using 0.1 N sodium hydroxide and/or 0.1 N hydrochloric acid, as necessary.

The pH of 750 ml of the triethanolamine stock solution was adjusted to 9.0±0.1 using 0.1 N sodium hydroxide and/or 0.1 N hydrochloric acid, as necessary.

2.2.1.3 0.1 M Phosphate Buffer 0.71 g±0.01 g of monosodium phosphate, monohydrate and 18.7±0.1 g disodium phosphate, heptahydrate were weighed and added to 750 mL of nanopure water. The mixture was mixed to form a solution 0.1 M phosphate buffer, pH 8.0±0.1.

2.2.1.4 LB-100 Formulations

For each of the buffer solutions above, 650 mL of a 1 mg/mL LB-100 solution was prepared by weighing and transferring 650 mg±10 mg of LB-100 (free acid) into a vessel containing 650 mL of the appropriate buffer. Using magnetic stirring, the mixtures were mixed until all LB-100 was completely dissolved. The pH of the solutions were checked and adjusted hack into the stated range of the buffer, if necessary, using 0.1 N sodium hydroxide or 0.1 N hydrochloric acid. The solutions were filtered through a 0.22 μm nylon membrane filter.

2.2.2 Filling and Storage of Vials

Using USP type I glass vials and teflon stoppers, 50 vials were filled for each solution. The vials were stored according to the conditions of Table 2.

TABLE 2

| Storage Condition | Orientation | Number of Vials |
|---|---|---|
| 25° C./60% | Upright | 5 |
| 25° C./60% | Inverted | 5 |
| 2 to 8° C. | Upright | 12 |
| 2 to 8° C. | Inverted | 12 |
| −20° C. | Upright | 12 |
| −20° C. | Inverted | 12 |

2.3 Results 2.3.1 Analysis at 1 Month

LB-100 concentrations were measured by HPLC at time zero and one month. Samples were visually inspected for the presence of particulates. Time zero results are shown in Table 3. One month results are shown in Tables 4-7.

TABLE 3

| Formulation | Analyzed Conc. (mg/mL) | Analyzed Conc. (mean) | Mean Conc. Percent of Target | Visual Observation |
|---|---|---|---|---|
| Glutamate Buffer, pH 8.5 ± 0.1 | 0.959 | 0.991 | 99.1 | No particulates |
| | 1.02 | | | No particulates |
| Glutamate Buffer, pH 10.5 ± 0.1 | 1.15 | 1.17 | 117 | No particulates |
| | 1.18 | | | No particulates |
| Triethanolamine Buffer, pH 7.0 ± 0.1 | 0.877 | 0.895 | 89.5 | No particulates |
| | 0.913 | | | No particulates |
| Triethanolamine Buffer, pH 9.0 ± 0.1 | 1.19 | 1.16 | 116 | No particulates |
| | 1.14 | | | No particulates |
| Phosphate Buffer, pH 8.0 ± 0.1 | 1.09 | 1.07 | 107 | No particulates |
| | 1.06 | | | No particulates |

TABLE 4

| Formulation | Analyzed Conc. (mg/mL) | Percent of Target | Percent of Time Zero | Visual Observation |
|---|---|---|---|---|
| Glutamate Buffer, pH 8.5 ± 0.1, 25° C./60%, Upright | 0.00509 | 0.509 | 0.514 | No particulates |
| Glutamate Buffer, pH 10.5 ± 0.1, 25° C./60%, Upright | 0.88 | 88.0 | 75.5 | No particulates |
| Triethanolamine Buffer, pH 7.0 ± 0.1, 25° C./60%, Upright | 0.0718 | 7.18 | 8.03 | No particulates |
| Triethanolamine Buffer, pH 9.0 ± 0.1, 25° C./60%, Upright | 0.563 | 56.3 | 48.4 | No particulates |
| Phosphate Buffer pH 8.0 ± 0.1, 25° C./60%, Upright | 0.287 | 28.7 | 26.7 | No particulates |

TABLE 5

| Formulation | Analyzed Conc. (mg/mL) | Percent of Target | Percent of Time Zero | Visual Observation |
|---|---|---|---|---|
| Glutamate Buffer, pH 8.5 ± 0.1, 25° C./60%, Inverted | .00353 | 0.353 | 0.356 | No particulates |
| Glutamate Buffer, pH 10.5 ± 0.1, 25° C./60%, Inverted | 0.950 | 95.0 | 81.5 | No particulates |
| Triethanolamine Buffer, pH 7.0 ± 0.1, 25° C./60%, Inverted | 0.0728 | 7.28 | 8.14 | No particulates |
| Triethanolamine Buffer, pH 9.0 ± 0.1, 25° C./60%, Inverted | 0.593 | 59.3 | 51.0 | No particulates |
| Phosphate Buffer, pH 8.0 ± 0.1, 25° C./60%, Inverted | 0.300 | 30.0 | 28.0 | No particulates |

TABLE 6

| Formulation | Analyzed Conc. (mg/mL) | Percent of Target | Percent of Time Zero | Visual Observation |
|---|---|---|---|---|
| Glutamate Buffer, pH 8.5 ± 0.1, 2-8° C., Upright | 0.704 | 70.4 | 71.0 | No particulates |
| Glutamate Buffer, pH 10.5 ± 0.1, 2-8° C., Upright | 0.978 | 97.8 | 83.9 | No particulates |
| Triethanolamine Buffer, pH 7.0 ± 0.1, 2-8° C., Upright | 0.372 | 37.2 | 41.6 | No particulates |
| Triethanolamine Buffer, pH 9.0 ± 0.1, 2-8° C., Upright | 0.975 | 97.5 | 83.8 | No particulates |
| Phosphate Buffer, pH 8.0 ± 0.1, 2-8° C., Upright | 0.864 | 86.4 | 80.5 | No particulates |

TABLE 7

| Formulation | Analyzed Conc. (mg/mL) | Percent of Target | Percent of Time Zero | Visual Observation |
|---|---|---|---|---|
| Glutamate Buffer, pH 8.5 ± 0.1, 2-8° C., Inverted | 0.645 | 64.5 | 65.1 | No particulates |
| Glutamate Buffer, pH 10.5 ± 0.1, 2-8° C., Inverted | 0.985 | 98.5 | 84.5 | No particulates |
| Triethanolamine Buffer, pH 7.0 ± 0.1, 2-8° C., Inverted | 0.374 | 37.4 | 41.8 | No particulates |
| Triethanolamine Buffer, pH 9.0 ± 0.1, 2-8° C., Inverted | 0.909 | 90.9 | 78.1 | No particulates |
| Phosphate Buffer, pH 8.0 ± 0.1, 2-8° C., Inverted | 0.838 | 83.8 | 78.1 | No particulates |

2.3.2 Analysis at 3 Months

LB-100 concentrations were measured by HPLC at three months for the top two performing formulations at one month (glutamate buffer, pH 10.5 and triethanolamine buffer, pH 9.0). Three month results for these formulations are shown in Table 8.

TABLE 8

| Formulation | Analyzed Conc. (mg/mL) | Analyzed Conc. (mean) | Mean Conc. Percent of Target | Visual Observation |
|---|---|---|---|---|
| Glutamate Buffer, pH 10.5 ± 0.1, 2-8° C. | 1.00<br>1.01 | 1.00 | 98.3 | Particulates were present |
| Triethanolamine Buffer, pH 9.0 ± 0.1, 2-8° C. | 0.858<br>0.783 | 0.820 | 81.1 | Particulates were present |
| Glutamate Buffer, pH 10.5 ± 0.1, −20° C. | 1.04<br>1.04 | 1.04 | 102 | No particulates |
| Triethanolamine Buffer, pH 9.0 ± 0.1, −20° C. | 0.982<br>0.914 | 0.948 | 93.8 | No particulates |

2.3.3 Analysis of Glutamate Buffer, pH 10.5 at 9 Months

The top performing formulation at 1 and 3 months (1 mg/mL LB-100 in 0.1 M glutamate buffer, pH 10.5) was selected for further analysis. Properties of the formulation following 1 month of storage at 5° C. 3° C. are shown in Table 9. Properties of the formulation following 1, 3, 6, and 9 months of storage at −20° C.±10° C. are shown in Table 10. A representative HPLC chromatogram of the formulation at 9 months is shown in FIG. 1.

TABLE 9

| Test | Initial Time Point | 1-Month Time Point |
|---|---|---|
| Appearance | Clear liquid free of any visible particulates | Clear liquid free of any visible particulate |
| pH | 10.3 | 10.4 |
| Assay by HPLC | 102.5% | 101.9% |
| Sterility (bacterial endotoxin | Meets USP 34 | n/a[1] |
| Particulate Matter | Meets USP 34 | n/a[1] |

[1]Testing not performed

TABLE 10

| Test | Initial Time Point | 1 Month Time Point | 3-Month Time Point | 6-Month Time Point | 9-Month Time Point |
|---|---|---|---|---|---|
| Appearance | Clear liquid free of any visible particulates | Clear liquid free of any visible particulates | Clear liquid free of any visible particulates | Clear liquid free of any visible particulates | Clear liquid free of any visible particulates |
| pH | 10.3 | 10.4 | 10.4 | 10.4 | 10.3 |
| Assay by HPLC | 102.5% | 102.7% | 103.9% | 101.3% | 101.1% |
| Sterility (bacterial endotoxin) | Meets USP 34 | n/a[1] | n/a[1] | n/a[1] | n/a[1] |
| Particulate Matter | Meets USP 34 | n/a[1] | n/a[1] | n/a[1] | n/a[1] |
| Impurities by HPLC | n/a[1] | n/a[1] | <LOQ[2] | <LOQ[2] | <LOQ[2] |

[1]Testing not performed;
[2]LOQ (Limit of Quantitation) = 2%

2.4 Discussion

Glutamate buffer, pH 10.5 was the clear standout among the tested formulations. The formulation of 1 mg/mL LB-100 in monosodium glutamate, pH 10.5, showed superior storage stability at one and three months at 25° C. and 2-8° C., and retained LB-100 potency up to and including 9 months of storage at −20° C.

Example 3. Pharmaceutical Composition Comprising LB-100

The following protocol is used to make 42 L of a pharmaceutical composition comprising 1 mg/mL LB-100 and 0.1M monosodium glutamate, pH 10.5.

3.1 Materials

TABLE 11

Formulation Ingredients

| Component | Amount |
|---|---|
| Sodium-L-Glutamate Monohydrate FCC, NF | 785.9 g |
| 5N Hydrochloric Acid, NF | As needed to adjust pH |
| 5N Sodium Hydroxide, NF | As needed to adjust pH |
| LB-100 | 42.00 g* |
| Sterile Water for Injection, USP | 42.5 kg** |

*Theoretical weight of LB-100 required. The actual amount of LB-100 added from a given lot should be determined based upon purity and moisture content of the lot.
**Batch size of 42,000 mL adjusted for formulation density of 1.012 g/mL

TABLE 12

Container and Closure Components

| Component | Type |
|---|---|
| Vial | 10 mL clear, 20 mm opening, USP Type 1 glass (Wheaton 223739) |
| Stopper | 20 mm, 4416/50, gray butyl, Telflon ®-2 coated (West 1014-4937) |
| Seal | 20 mm, 3766 white, 8-bridge flip-off (West 5420-3028) |

TABLE 13

Filter & Tubing Components

| Component | Type |
|---|---|
| Solution Filter | 4 inch Opticap, 0.22 micron Durapore ® sterile (Millipore KVGLS4HH3) |
| Peristaltic Pump Tubing | 0.375 inch ID × 0.625 inch OD, Pharma 50 Silastic ® (Dow Corning 3100499) |
| Filter Outlet Tubing | 0.375 inch ID × 0.563 inch OD, Pharma 50 Silastic ® (Dow Corning 3100481) |
| Flexicon 3.2 Tubing | 0.125 inch ID × 0.250 inch OD, Pharma 50 Silastic ® (Dow Corning 3100430) |

3.2 Formulation Manufacturing Process

Approximately 34 kg of the Sterile Water for Injection, USP is added to a 40 L glass carboy. The Sodium-L-Glutamate Monohydrate is then added to the carboy and mixed for a minimum of ten minutes. The pH of the resulting mixture is adjusted with the sodium hydroxide and/or hydrochloric acid to a pH within the range 10.4-10.6. The target pH for this pH adjustment step is 10.5. Mixing of the mixture is continued until all of the solids in the carboy are dissolved.

Next, the LB-100 is added to the carboy and mixed for a minimum of ten minutes or until all of the LB-100 is dissolved. The pH of the resulting mixture is adjusted with the sodium hydroxide and/or hydrochloric acid to a pH within the range 10.4-10.6. The target pH for this pH adjustment step is 10.5. Mixing of the mixture is continued until all of the solids in the carboy are dissolved.

Next, Sterile Water for Injection is added to the carboy to bring the total weight of the mixture to 42.5 kg. The mixture is stirred for a minimum of five minutes to give a solution of 1 mg/mL LB-100 in 0.1M monosodium glutamate, pH 10.5.

Next, the solution is sterile filtered using the solution filter to provide a sterile solution of 1 ma/mL LB-100 in 0.1M monosodium glutamate, pH 10.5.

Finally, the vials are each filled with approximately 10 mL of the sterile solution (10.63 g±0.21 g) and stoppered.

3.3 Discussion

The manufacturing process described in Example 3 allows for the production of 42 L of 1 mg/mL LB-100 in 0.1M monosodium glutamate, pH 10.5. Larger and smaller batches can be readily obtained by adjusting the amounts of components as necessary to obtain the desired batch size. It should be appreciated that variations in the above-described steps may be necessary when adjusting the batch size, e.g. necessary mixing times may be longer or shorter depending upon batch size and equipment used to prepare the batch.

The pharmaceutical composition comprising 1 mg/mL LB-100 in 0.1M monosodium glutamate, pH 10.5, made by the process of Example 3 is stable for months at −20° C. and for at least 8 hours at refrigerated temperatures. The stability of this pharmaceutical composition allows for it to be commercially manufactured, shipped, and stored for a prolonged amount of time without a significant amount of degradation. In the clinical setting, it may be desirable to add the amount of the pharmaceutical solution which is to be administered to a subject to a pharmaceutically acceptable carrier prior to administration to a subject. For example, the pharmaceutical composition can be diluted in normal saline in order to reduce the pH of the pharmaceutical composition immediately before administration.

The therapeutic benefit of treating cancer with the pharmaceutical composition comprising LB-100 may be further enhanced by combining treatment with the pharmaceutical composition with other anti-cancer treatments including ionizing radiation and agents used for the treatment of cancer that induce abnormalities in DNA and/or that interfere with one or more constituents of the mitotic process. In particular, the anti-cancer activity of X-ray, DNA alkylating agents, DNA intercalating agents, and microtubule stabilizing and disrupting agents may be enhanced by treatment with the pharmaceutical composition comprising LB-100. The addition of spindle poisons and/or x-ray during or following exposure of cancers to the pharmaceutical composition comprising LB-100 may enhance the extent of cancer cell killing without increasing toxicity to normal cells. Specifically, combinations of the pharmaceutical composition comprising LB-100 with ionizing radiation (X-ray therapy), spindle poisons including taxol, vincristine (VCR), vinblastine (VBL), and/or DNA damaging agents including anthracyclines, bleomycin, cisplatin, etoposide, temozolomide, and nitrosoureas may be more effective anti-cancer regimens than standard regimens of single anti-cancer agents or combinations of agents in the absence of treatment with the pharmaceutical composition comprising LB-100. This list of anti-cancer drugs is not meant to be inclusive of all drugs that may be combined to advantage with the pharmaceutical composition comprising LB-100. Because the mechanism of action of LB-100 on TCTP and other regulatory molecules is distinct from all other approved anti-cancer regimens, the pharmaceutical composition comprising LB-100 may be used to advantage in combination with any of all FDA approved cancer regimens (for list of FDA-approved anti-cancer drugs see: www.accessdata.fda.gov.gov.scripts/cder/onctools/druglist.cfm).

It should also be appreciated that pharmaceutical compositions comprising PP2A inhibitors other than LB-100 can be produced using the process described in Example 3 by substituting the amount of LB-100 for an appropriate amount of another PP2A inhibitor.

REFERENCES

Lu, J. et al., "The effect of a PP2A inhibitor on the nuclear receptor corepressor pathway in glioma," J. Neurosurg. Vol. 113(2):225-33 (2010);

Martiniova, L. et al., "Pharmacologic modulation of serine/threonine phosphorylation highly sensitizes PHEO in a MPC cell and mouse model to conventional chemotherapy," PLoS One vol. 6(2):e14678 (2011);

PCT International Application Publication No. WO 2008/097561 (Kovach & Johnson), published Aug. 14, 2008;

PCT International Application Publication No. WO 2009/020565 (Kovach & Zhuang), published Feb. 12, 2009;

PCT International Application Publication No. WO 2010/014141 (Kovach et al.), published Feb. 4, 2010;

PCT International Application Publication No. WO 2010/014220 (Kovach), published Feb. 4, 2010;

PCT International Application Publication No WO 2010/014254 Kovach & Johnson), published Feb. 4, 2010;

PCT International Application Publication No. WO 2010/147612 (Kovach), published Dec. 23, 2010;

PCT International Application Publication No. WO 2012/162535 (Kovach et al.), published Nov. 29, 2012;

U.S. Provisional Application No. 61/782,894 (Kovach), filed Mar. 14, 2013

Zhang, C. et al., "A synthetic cantharidin analog for the enhancement of doxorubicin suppression of stem cell-derived aggressive sarcoma," Biomaterials, vol. 31(36) 9535-43 (2010).

What is claimed is:

1. A pharmaceutical composition comprising a protein phosphatase 2A inhibitor and monosodium glutamate, wherein the protein phosphatase 2A inhibitor has the structure:

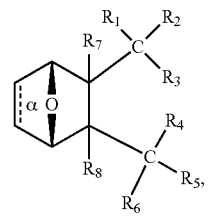

wherein:
bond α is present or absent;
$R_1$ and $R_2$ is each independently H, O⁻ or $OR_9$, or $R_1$ and $R_2$ together are =O;
each $R_9$ is independently H, alkyl, alkenyl, alkynyl or aryl;
$R_3$ and $R_4$ are each different, and each is OH, O⁻, $OR_9$, SH, S, $SR_9$,

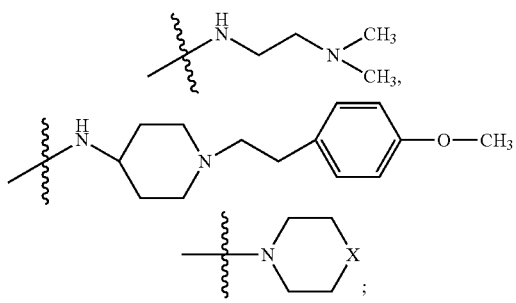

X is $NR_{10}$, or $N^+R_{10}R_{10}$;

each $R_{10}$ is independently H, alkyl, substituted $C_2$-$C_{12}$ alkyl, alkenyl, substituted $C_4$-$C_{12}$ alkenyl, alkynyl, substituted alkynyl, aryl, substituted aryl where the substituent is other than chloro when $R_1$ and $R_2$ are =O, —$CH_2CN$, —$CH_2CO_2R_{11}$, —$CH_2COR_{11}$, —$NHR_{11}$ or —$NH^+(R_{11})_2$;

each $R_{11}$ is independently H or a substituted or unsubstituted group selected from alkyl, alkenyl or alkynyl;

$R_5$ and $R_6$ is each independently H, OH, or $R_5$ and $R_6$ taken together are =O;

$R_7$ and $R_8$ is each independently H, F, Cl, Br, $SO_2Ph$, $CO_2CH_3$, or $SR_{12}$; and each $R_{12}$ is independently H, aryl, or a substituted or unsubstituted group selected from alkyl, alkenyl or alkynyl;

or a salt, enantiomer or zwitterion of the protein phosphatase 2A inhibitor; and wherein the pharmaceutical composition has a pH of 10-11.

2. The pharmaceutical composition of claim 1, wherein the protein phosphatase 2A inhibitor has the structure:

wherein:

bond α is present or absent;

$R_9$ is present or absent and when present is H, alkyl, alkenyl, alkynyl or phenyl;

X is $NR_{10}$, or $N^+R_{10}R_{10}$;

each $R_{10}$ is independently H, alkyl, substituted $C_2$-$C_{12}$ alkyl, alkenyl, substituted $C_4$-$C_{12}$ alkenyl, alkynyl, substituted alkynyl, aryl, substituted aryl where the substituent is other than chloro, —$CH_2CN$, —$CH_2CO_2R_{12}$, or —$CH_2COR_{12}$; and each $R_{12}$ is independently H or alkyl;

or a salt, zwitterion, or enantiomer of the protein phosphatase 2A inhibitor.

3. The pharmaceutical composition of claim 1, wherein the protein phosphatase 2A inhibitor has the structure

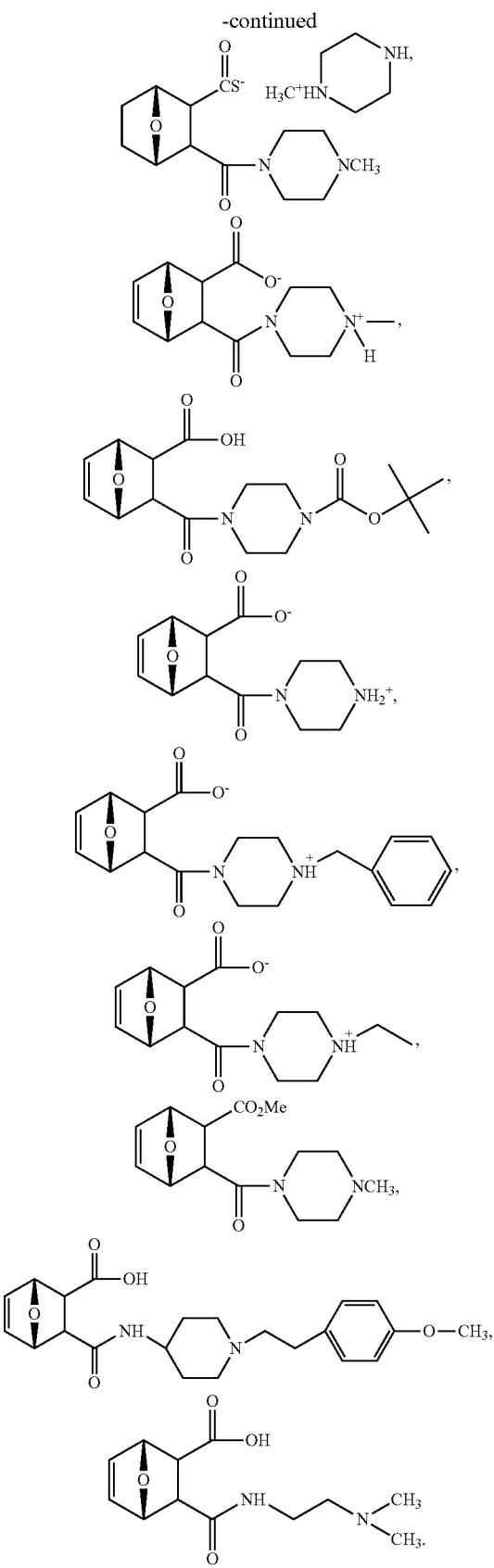

4. The pharmaceutical composition of claim 1, wherein the protein phosphatase 2A inhibitor has the structure:

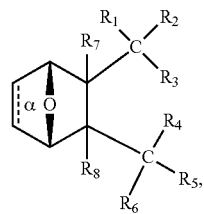

wherein
bond α is present or absent;
$R_1$ and $R_2$ is each independently H, $O^-$ or $OR_9$, or $R_1$ and $R_2$ together are =O;
each $R_9$ is independently H, alkyl, substituted alkyl, alkenyl, alkynyl or aryl;
$R_3$ and $R_4$ are each different, and each is $O(CH_2)_{1-6}R_9$ or $OR_{10}$, or

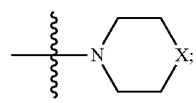

X is $NR_{11}$, or $N^+R_{11}R_{11}$;
$R_{10}$ is substituted alkyl, substituted alkenyl, substituted alkynyl, or substituted aryl;
each $R_{11}$ is independently H, alkyl, hydroxyalkyl, substituted $C_2$-$C_{12}$ alkyl, alkenyl, substituted $C_4$-$C_{12}$ alkenyl, alkynyl, substituted alkynyl, aryl, substituted aryl where the substituent is other than chloro when $R_1$ and $R_2$ are =O,

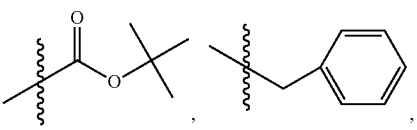

—$CH_2CN$, —$CH_2CO_2R_{12}$, —$CH_2COR_{12}$, —$NHR_{12}$ or —$NH^+(R_{12})_2$;
each $R_{12}$ is independently H or a substituted or unsubstituted group selected from alkyl, alkenyl or alkynyl;
or a salt, enantiomer or zwitterion of the protein phosphatase 2A inhibitor.

5. The pharmaceutical composition of claim 3, wherein the protein phosphatase 2A inhibitor has the structure

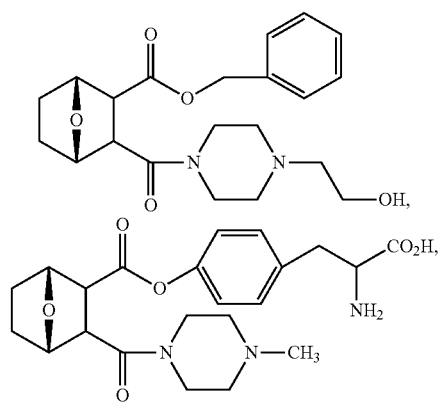

-continued

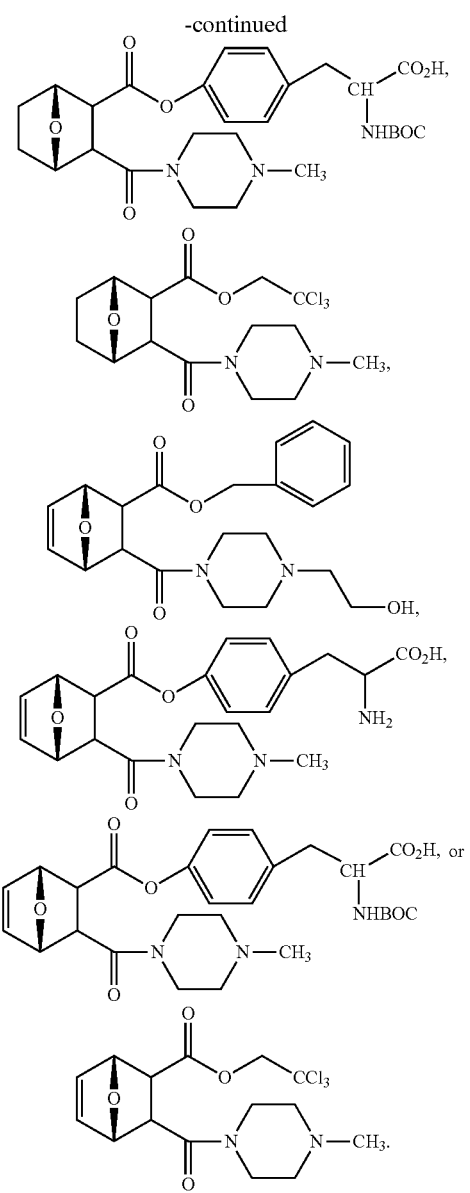

6. The pharmaceutical composition of claim 1, wherein the protein phosphatase 2A inhibitor has the structure

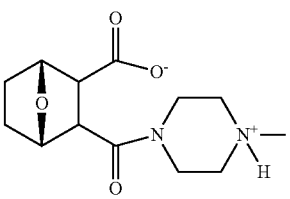 [SMILES: C[NH+]1CCN(C(=O)C2C(C(=O)[O-])[C@H]3CC[C@@H]2O3)CC1]

or a salt or enantiomer thereof.

7. The pharmaceutical composition of claim 1, further comprising water.

8. The pharmaceutical composition of claim 1, wherein the pH of the pharmaceutical composition is 10.5.

9. The pharmaceutical composition of claim 7, wherein the protein phosphatase 2A inhibitor is present in the pharmaceutical composition at a concentration of 1.0 mg/mL and/or the monosodium glutamate is present in the pharmaceutical composition at a concentration of 0.1 M.

10. A sealed package comprising the pharmaceutical composition of claim 1.

11. A method of preparing a pharmaceutical composition for administration to a subject, comprising mixing an amount of the pharmaceutical composition of claim 1 with a saline solution.

12. A method of making the pharmaceutical composition of claim 1, comprising a) adding an amount of monosodium glutamate to an amount of water to form a mixture of monosodium glutamate and water; and b) adding an amount of a protein phosphatase 2 inhibitor to the mixture;

and optionally further comprising a step of adjusting the pH of the mixture after step (a), a step or adjusting the pH of the mixture after step (b), or a step of adjusting the pH of the mixture after step (a) and a step of adjusting the pH of the mixture after step (b), wherein the pH of the mixture is adjusted to a pH range of 10-11 in each pH adjusting step.

* * * * *

UNITED STATES PATENT AND TRADEMARK OFFICE
CERTIFICATE OF CORRECTION

| | | |
|---|---|---|
| PATENT NO. | : 10,532,050 B2 | Page 1 of 1 |
| APPLICATION NO. | : 14/783360 | |
| DATED | : January 14, 2020 | |
| INVENTOR(S) | : John S. Kovach et al. | |

It is certified that error appears in the above-identified patent and that said Letters Patent is hereby corrected as shown below:

In the Specification

At Column 25, Line 37, replace "unsubstituted or unsubstituted" with -- substituted or unsubstituted --

In the Claims

At Column 42, Line 48, replace "claim 3" with -- claim 1 --

Signed and Sealed this
Twenty-ninth Day of March, 2022

Drew Hirshfeld
*Performing the Functions and Duties of the*
*Under Secretary of Commerce for Intellectual Property and*
*Director of the United States Patent and Trademark Office*